United States Patent
Mallery et al.

(10) Patent No.: US 11,033,496 B2
(45) Date of Patent: Jun. 15, 2021

(54) NANOPARTICLES FOR DELIVERY OF CHEMOPREVENTIVE AGENTS

(71) Applicants: OHIO STATE INNOVATION FOUNDATION, Columbus, OH (US); THE REGENTS OF THE UNIVERSITY OF MICHIGAN, Ann Arbor, MI (US)

(72) Inventors: Susan R. Mallery, Columbus, OH (US); Joerg Lahann, Ann Arbor, MI (US)

(73) Assignees: THE REGENTS OF THE UNIVERSITY OF MICHIGAN, Ann Arbor, MI (US); OHIO STATE INNOVATION FOUNDATION, Columbus, OH (US)

(*) Notice: Subject to any disclaimer, the term of this patent is extended or adjusted under 35 U.S.C. 154(b) by 0 days.

(21) Appl. No.: 16/494,995

(22) PCT Filed: Mar. 16, 2018

(86) PCT No.: PCT/US2018/022877
§ 371 (c)(1),
(2) Date: Sep. 17, 2019

(87) PCT Pub. No.: WO2018/170405
PCT Pub. Date: Sep. 20, 2018

(65) Prior Publication Data
US 2020/0038327 A1    Feb. 6, 2020

Related U.S. Application Data

(60) Provisional application No. 62/575,683, filed on Oct. 23, 2017, provisional application No. 62/473,015, filed on Mar. 17, 2017.

(51) Int. Cl.
*A61K 36/73* (2006.01)
*A61K 47/62* (2017.01)
(Continued)

(52) U.S. Cl.
CPC .......... *A61K 9/1647* (2013.01); *A61K 9/006* (2013.01); *A61K 9/0014* (2013.01); *A61K 9/06* (2013.01);
(Continued)

(58) Field of Classification Search
CPC ...... A61K 47/62; A61K 31/00; A61K 31/167; A61K 31/198; A61K 36/73;
(Continued)

(56) References Cited

U.S. PATENT DOCUMENTS 5,171,840 A    12/1992 Kishimoto
5,480,796 A    1/1996 Kishimoto
(Continued)

FOREIGN PATENT DOCUMENTS

WO           00/10607       3/2000
WO           2011/013786    2/2011
WO           WO-2017147169 A1 *  8/2017  ......... A61K 39/3955

OTHER PUBLICATIONS

Rahmani et al. (J Drug Target. 2015;23(7-8):750-758) (Year: 2015).*
(Continued)

*Primary Examiner* — Ernst V Arnold
(74) *Attorney, Agent, or Firm* — Harness, Dickey & Pierce, P.L.C.

(57) ABSTRACT

Disclosed herein are nanoparticle compositions and methods of use such as for chemoprevention of cancer, for example oral squamous cell carcinoma (OSCC). The nanoparticle composition comprises a Janus particle comprising at least two chemopreventive agents, wherein at least one of the chemopreventive agents is selected from freeze-dried black
(Continued)

raspberries (BRB), a synthetic vitamin A analogue, N-acetylcysteine (NAC), and an anti-interleukin 6 agent. Methods for improving oral health comprising administering to a subject the nanoparticle compositions are also disclosed.

24 Claims, 11 Drawing Sheets

(51) Int. Cl.
| | |
|---|---|
| A61K 47/69 | (2017.01) |
| A61K 9/16 | (2006.01) |
| A61K 9/00 | (2006.01) |
| A61K 9/06 | (2006.01) |
| A61K 31/167 | (2006.01) |
| A61K 31/198 | (2006.01) |
| A61K 39/395 | (2006.01) |

(52) U.S. Cl.
CPC .......... *A61K 31/167* (2013.01); *A61K 31/198* (2013.01); *A61K 36/73* (2013.01); *A61K 39/3955* (2013.01); *A61K 47/62* (2017.08); *A61K 47/6929* (2017.08); *A61K 47/6937* (2017.08)

(58) Field of Classification Search
CPC ............ A61K 39/3955; A61K 47/6849; A61K 47/6927; A61K 47/6929; A61K 47/6937; A61K 9/0014; A61K 9/006; A61K 9/06; A61K 9/1647; A61P 1/02; A61P 35/00
See application file for complete search history.

(56) References Cited

U.S. PATENT DOCUMENTS

| | | | |
|---|---|---|---|
| 5,670,373 | A | 9/1997 | Kishimoto |
| 5,795,965 | A | 8/1998 | Tsuchiya et al. |
| 5,817,790 | A | 10/1998 | Tsuchiya et al. |
| 5,851,793 | A | 12/1998 | Kishimoto |
| 5,888,510 | A | 3/1999 | Kishimoto et al. |
| 5,990,282 | A | 11/1999 | Kishimoto |
| 6,086,874 | A | 7/2000 | Yoshida et al. |
| 6,261,560 | B1 | 7/2001 | Tsujinaka et al. |
| 6,410,691 | B1 | 6/2002 | Kishimoto |
| 6,428,979 | B1 | 8/2002 | Kishimoto |
| 6,537,782 | B1 | 3/2003 | Shibuya et al. |
| 6,692,742 | B1 | 2/2004 | Nakamura et al. |
| 6,723,319 | B1 | 4/2004 | Ito et al. |
| 6,962,812 | B2 | 11/2005 | Shibuya et al. |
| 7,320,792 | B2 | 1/2008 | Ito et al. |
| 7,332,289 | B2 | 2/2008 | Takeda et al. |
| 7,479,543 | B2 | 1/2009 | Tsuchiya et al. |
| 7,521,052 | B2 | 4/2009 | Okuda et al. |
| 7,566,453 | B2 | 7/2009 | Nakamura et al. |
| 7,767,017 | B2 | 8/2010 | Lahann et al. |
| 7,771,723 | B2 | 8/2010 | Nakamura et al. |
| 7,824,674 | B2 | 11/2010 | Ito et al. |
| 7,927,815 | B2 | 4/2011 | Takeda et al. |
| 7,947,772 | B2 | 5/2011 | Lahann et al. |
| 7,955,598 | B2 | 6/2011 | Yoshizaki et al. |
| 8,043,480 | B2 | 10/2011 | Lahann et al. |
| 8,187,708 | B2 | 5/2012 | Lahann et al. |
| 8,273,385 | B1 | 9/2012 | Shine |
| 2001/0001663 | A1 | 5/2001 | Kishimoto et al. |
| 2002/0131967 | A1 | 9/2002 | Nakamura et al. |
| 2002/0187150 | A1 | 12/2002 | Mihara et al. |
| 2003/0096372 | A1 | 5/2003 | Shibuya et al. |
| 2003/0190316 | A1 | 10/2003 | Kakuta et al. |
| 2004/0028681 | A1 | 2/2004 | Ito et al. |
| 2004/0071706 | A1 | 4/2004 | Ito et al. |
| 2004/0115197 | A1 | 6/2004 | Yoshizaki et al. |
| 2004/0138424 | A1 | 7/2004 | Takeda et al. |
| 2004/0247621 | A1 | 12/2004 | Nakamura et al. |
| 2005/0031550 | A1 | 2/2005 | Busch |
| 2005/0118163 | A1 | 6/2005 | Mizushima et al. |
| 2005/0142635 | A1 | 6/2005 | Tsuchiya et al. |
| 2005/0214278 | A1 | 9/2005 | Kakuta et al. |
| 2005/0238644 | A1 | 10/2005 | Mihara et al. |
| 2006/0134113 | A1 | 6/2006 | Mihara |
| 2006/0142549 | A1 | 6/2006 | Takeda et al. |
| 2006/0165696 | A1 | 7/2006 | Okano et al. |
| 2006/0251653 | A1 | 11/2006 | Okuda et al. |
| 2006/0292147 | A1 | 12/2006 | Yoshizaki et al. |
| 2007/0036785 | A1 | 2/2007 | Kishimoto et al. |
| 2007/0098714 | A1 | 5/2007 | Nishimoto et al. |
| 2007/0134242 | A1 | 6/2007 | Nishimoto et al. |
| 2007/0148169 | A1 | 6/2007 | Yoshizaki et al. |
| 2007/0243189 | A1 | 10/2007 | Yoshizaki et al. |
| 2008/0124325 | A1 | 5/2008 | Ito et al. |
| 2008/0124761 | A1 | 5/2008 | Goto et al. |
| 2008/0255342 | A1 | 10/2008 | Takeda et al. |
| 2008/0274106 | A1 | 11/2008 | Nishimoto et al. |
| 2008/0306247 | A1 | 12/2008 | Mizushima et al. |
| 2009/0022719 | A1 | 1/2009 | Mihara et al. |
| 2009/0131639 | A1 | 5/2009 | Kakuta et al. |
| 2009/0181029 | A1 | 7/2009 | Okuda et al. |
| 2009/0220499 | A1 | 9/2009 | Yasunami |
| 2009/0220500 | A1 | 9/2009 | Kobara |
| 2009/0263384 | A1 | 10/2009 | Okada et al. |
| 2009/0269335 | A1 | 10/2009 | Nakashima et al. |
| 2009/0280183 | A1* | 11/2009 | Lizio .................. A61K 31/7088 424/487 |
| 2009/0291076 | A1 | 11/2009 | Morichika et al. |
| 2010/0008907 | A1 | 1/2010 | Nishimoto et al. |
| 2010/0034811 | A1 | 2/2010 | Ishida |
| 2010/0061986 | A1 | 3/2010 | Takahashi et al. |
| 2010/0129355 | A1 | 5/2010 | Ohguro et al. |
| 2010/0247523 | A1 | 9/2010 | Kano et al. |
| 2010/0255007 | A1 | 10/2010 | Mihara et al. |
| 2010/0285011 | A1 | 11/2010 | Morichika et al. |
| 2010/0304400 | A1 | 12/2010 | Stubenrach et al. |
| 2011/0117087 | A1 | 5/2011 | Franze et al. |
| 2011/0150869 | A1 | 6/2011 | Mitsunaga et al. |
| 2014/0234212 | A1* | 8/2014 | Goldberg ............... A61K 9/006 424/1.25 |

OTHER PUBLICATIONS

International Search Report and Written Opinion issued by the International Searching Authority (ISA/US) in PCT Application No. PCT/US2018/022877 dated Jun. 11, 2019. 17 pages.
Desai, Kashappa Goud H., et al. "Formulation and in vitro-in vivo evaluation of black raspberry extract-loaded PLGA/PLA injectable millicylindrical implants for sustained delivery of chemopreventive anthocyanins." Pharmaceutical research 27.4 (2010): 628-643.
Holpuch, Andrew S., et al. "Optimizing therapeutic efficacy of chemopreventive agents: A critical review of delivery strategies in oral cancer chemoprevention clinical trials." Journal of carcinogenesis 10(23) (2011): 1-17.
Kumari, Neeraj, et al. "Role of interleukin-6 in cancer progression and therapeutic resistance." Tumor Biology 37.9. (2016): 11553-11572.
Mallery, Susan R., et al. "Formulation and in-vitro and in-vivo evaluation of a mucoadhesive gel containing freeze dried black raspberries: implications for oral cancer chemoprevention." Pharmaceutical research 24.4 (2007): 728-737.
Mallery, Susan R., et al. "Topical application of a mucoadhesive freeze-dried black raspberry gel induces clinical and histologic regression and reduces loss of heterozygosity events in premalignant oral intraepithelial lesions: results from a multicentered, placebo-controlled clinical trial." Clinical Cancer Research 20.7 (2014): 1910-1924.
Mallery, Susan R., et al. "Benefits of multifaceted chemopreventives in the suppression of the oral squamous cell carcinoma (OSCC) tumorigenic phenotype." Cancer Prevention Research 10.1 (2017): 76-88.
The Ohio State University. "Oral Cancer Chemopreventive Rinse." (2016): 1-5.

(56) References Cited

OTHER PUBLICATIONS

Alter BP, Giri N, Savage SA, Quint WG, de Koning MN et al. Squamous cell carcinomas in patients with Fanconi anemia and dyskeratosis congenita: A search for human papillomavirus. Int J Cancer 2013, 133: 1513-1515.

Andrew S. Holpuch, Garrett J. Hummel, Meng Tong, Garrett A. Seghi, Ping Pei, Ping Ma, Russell J. Mumper, Susan R. Mallery Nanoparticles for Local Drug Delivery to the Oral Mucosa: Proof of Principle Studies. Pharm Res. 2010, 27, 1224-1236.

Andrew S. Holpuch, et al., Evaluation of a mucoadhesive fenretinide patch for local intraoral delivery: a strategy to reintroduce fenretinide for oral cancer chemoprevention. Carcinogenesis. 2012 33: 1098-1105.

Bhaskar, S.; Hitt, J.; Chang, S.-W. L.; Lahann, J. Multicompartmental Microcylinders. Angew. Chem. Int. Ed. 2009, 48, 4589.

Bhaskar, S.; Lahann, J. Microstructured Materials Based on Multicompartmental Fibers. J. Am. Chem. Soc. 2009, 131, 6650.

Bhaskar, S.; Pollock, K. M.; Yoshida, M.; Lahann, J. Towards Designer Microparticles: Simultaneous Control of Anisotropy, Shape, and Size. Small. 2010, 6, 404.

Byungdo B. Han, et al., Fenretinide Perturbs Focal Adhesion Kinase in Premalignant and Malignant Human Oral Keratinocytes. Fenretinide's Chemopreventive Mechanisms Include ECM Interactions. Cancer Prev Res. 2015, 8: 419-430.

Carter, Paul J. Introduction to current and future protein therapeutics: a protein engineering perspective. Experimental cell research 317.9 (2011): 1261-1269.

Chou TC, Drug Combination Studies and Their Synergy Quantification Using the Chou-Talalay Method. Cancer Res 70: 440-446, 2010.

Eva Müssig, Thorsten Steinberg, Annette Kohl, Walee Chamulitrat, Gerda Komposch and Pascal Tomakidi. Discrimination of epithelium-like and fibroblast-like phenotypes derived from ethanol-treated immortalised human gingival keratinocytes in epithelial equivalents. Cell Tissue Res. 2008, 332: 57-71.

Bayburt, Timothy H., and Stephen G. Sligar. "Membrane protein assembly into Nanodiscs." FEBS letters 584.9 (2010): 1721-1727.

Gary David Stoner, Li-Shu Wang and Bruce Cordell Casto. Laboratory and clinical studies of cancer chemoprevention by antioxidants in berries. Carcinogenesis 2008, 29: 1665-1674.

Hail N Jr, Kim HJ, Lotan R. Mechanisms of fenretinide-induced apoptosis. Apoptosis 11: 1677-1694, 2006.

Hecht, S.S. Chuanshu Huang, Gary D. Stoner, Jingxia Li, Patrick M.J. Kenney, Shana J. Sturla and Steven G. Carmella (2006) Identification of cyanidin glycosides as constituents of freeze-dried black raspberries which inhibit anti-benzo(a)pyrene-7,8- diol-9,10-epoxide induced NFκB and AP-1 activity. Carcinogenesis 2006, 27, 1617-1626.

Hoskins EE, Gunawardena RW, Habash KB, Wise-Draper TM, Jansen M et al. Coordinate regulation of Fanconi anemia gene expression occurs through the Rb/E2F pathway. Oncogene 2008, 27: 4798-4808.

Houghtaling S, Granville L, Akkari Y, Torimaru Y, Olson S, Finegold M, et al. Heterozygosity for p53 (Trp+/−) accelerates epithelial tumor formation in Fanconi anemia complementation group D2 (Fancd2) knockout mice. Cancer Res 2005;65:85-91.

Oral Cancer Facts 2019. http://oralcancerfoundation.org/facts/.

Understanding Your GIST Pathology Report Gastrointestinal Stromal Tumor 2010. http://www.gistsupport.org/for-new-gist-patients/understanding-yourpathology-report-for-gist/diagnosing-gist.php.

Joseph B. Guttenplan, Wieslawa Kosinska, Zhong-Lin Zhao, Kun-Ming Chen, Cesar Aliaga, Joseph DelTondo, Timothy Cooper, Yuan-Wan Sun3, Shang-Min Zhang, Kun Jiang, Richard Bruggeman, Arun K. Sharma, Shantu Amin, Kwangmi Ahn and Karam El-Bayoumy. Mutagenesis and carcinogenesis induced by dibenzo[a,l]pyrene in the mouse oral cavity: a potential new model for oral cancer. Int J Cancer 2011, 130: 2783-2790.

Jovanociv A, Schulten EAJM, Kostense PJ, Snow GB, van der Waal I. Tobacco and alcohol related to the anatomical site of oral squamous cell carcinoma. J Oral Pathol Med1993, 22: 459-462.

Jung Wook Park, Henry C. Pitot, Katerina Strati, Nicole Spardy, Stefan Duensing, Markus Grompe, and Paul F. Lambert. Deficiencies in the Fanconi Anemia DNA Damage Response Pathway Increase Sensitivity to HPV-Associated Head and Neck Cancer. Cancer Res. 2010, 70: 9959-9968.

Jung Wook Park, Myeong-Kyun Shin, Henry C. Pitot, Paul F. Lambert. High Incidence of HPV-Associated Head and Neck Cancers in FA Deficient Mice Is Associated with E7's Induction of DNA Damage through Its Inactivation of Pocket Proteins. PLOS One, 2013, 8: e75056.

Kashappa-Goud H. Desai & Susan R. Mallery & Andrew S. Holpuch & Steven P. Schwendeman. Development and In Vitro-In Vivo Evaluation of Fenretinide-Loaded Oral Mucoadhesive Patches for Site-Specific Chemoprevention of Oral Cancer. Pharm Res 28: 2599-2609, 2011.

Knipscheer P, Räschle M, Smogorzewska A, Enoiu M, Ho TV et al. The Fanconi anemia pathway promotes replication-dependent DNA interstrand cross-link repair. Science. 2009,326: 1698-1701.

Kreimer AR, Clifford GM, Boyle P, Franceschi S. Human papillomavirus types in head and neck squamous cell carcinomas worldwide: a systematic review. Cancer Epidemiol Biomarkers Prev2005,14(2):467-75.

Kujan O, Oliver RJ, Khattab A, Roberts SA, Thakker N, Sloan P. Evaluation of a new binary system of grading oral epithelial dysplasia for prediction of malignant transformation. Oral Oncology 42: 987-993, 2006.

Kun-Ming Chen, Joseph B. Guttenplan, Shang-Min Zhang, Cesar Aliaga, Timothy K. Cooper, Yuan-Wan Sun, Joseph DelTondo, Wieslawa Kosinska, Arun K. Sharma, Kun Jiang, Richard Bruggeman, Kwangmi Ahn, Shantu Amin and Karam El-Bayoumy. Mechanisms of oral carcinogenesis induced by dibenzo[a,1]pyrene: An environmental pollutant and a tobacco smoke constituent Internat J Cancer. 2013. 33: 1300-1309.

Kutler DI, Wreesmann VB, Goberdhan A, Ben-Porat L, Satagopan J et al. Human papillomavirus DNA and p53 polymorphisms in squamous cell carcinomas from Fanconi anemia patients. J Natl Cancer Inst 2003, 95: 1718-1721.

Kutler, DI, Auerbach AD, Satagopan J, Giampietro PF, Batish SD, Huvos AG, Goberdhan A, Shan JP, Singh B. High Incidence of Head and Neck Squamous Cell Carcinoma in Patients with Fanconi Anemia. Arch Oto Head Neck Surg 2003; 129: 106-112.

Lahann, J. Recent Progress in Nanobiotechnology: Compartmentalized Micro- and Nanoparticles via Electrohydrodynamic Co-jetting. Small. 2011, 7, 1149.

Laura A. Kresty, Mark A. Morse, Charlotte Morgan, Peter S. Carlton, Jerry Lu, Ashok Gupta, Michelle Blackwood and Gary D. Stoner. Chemoprevention of Esophageal Tumorigenesis by Dietary Administration of Lyophilized Black Raspberries. Cancer Res 2001, 61: 6112-6119.

Lee, K.J.; Yoon, J.; Lahann, J. Recent advances with anisotropic particles. Current Opinion in Colloid & Interface Science. 2011, 16, 195.

Lim, D. W., Hwang, S., Uzun, O., Stellacci, F. & Lahann, J. Compartmentalization of gold nanocrystals in polymer microparticles using electrohydrodynamic co-jetting. Macromol. Rapid Commun. 31, 176-182 (2010).

Mallery SR, Zwick JC, Pei P, Tong M, Larsen PE, Shumway BS, Lu B, Fields HW, Mumper RJ, Stoner GD. Topical Application of a Bioadhesive Black Raspberry Gel Modulates Gene Expression and Reduces Cyclooxygenase 2 Protein in Human Premalignant Oral Lesions. Cancer Res 2008,68: 4945-4957.

Meyer UA, Znger UM. Molecular Mechanisms of Genetic Polymorphisms of Drug Metabolism. Annu. Rev. Pharmacol. Toxicl. 1997, 37: 269-296.

Michaell A. Huber, Bundhit Tantiwongkosi. Oral and Oropharyngeal Cancer. Med Clin N Am 98 2014, 1299-1321.

Misra, A. C., Bhaskar, S., Clay, N. & Lahann, J. Multicompartmental particles for combined imaging and siRNA delivery. Adv. Mater. 24, 3850-3856 (2012).

Misra, A. C., Luker, K. E., Durmaz, H., Luker, G. D. & Lahann, J. CXCR4-Targeted Nanocarriers for Triple Negative Breast Cancers. Biomacromolecules 16, 2412-2417 (2015).

(56) References Cited

OTHER PUBLICATIONS

Park, Tae-Hong, et al. "Photoswitchable particles for on-demand degradation and triggered release." Small 9.18 (2013): 3051-3057.
Rahmani S. Ashraf S. Hartmann R. Dishman AF. Zyuzin M, Yu CKJ, Parak WJ, Lahann J. Engineering of nanoparticle size via electrohydrodynamic jetting. AlChE. Bioeng Tranl Med. 2016 1: 82-93.
Rahmani, S. et al. Chemically orthogonal three-patch microparticles. Angew. Chemie—Int. Ed. 53, 2332-2338 (2014).
Rahmani, S., Park, T. H., Dishman, A. F. & Lahann, J. Multimodal delivery of irinotecan from microparticles with two distinct compartments. J. Control. Release 172, 239-245 (2013).
Roh K-H, Martin DC, Lahann J. Biphasic Janus Particles with nanoscale anisotropy. Nature Material. 2005, 4: 759-763.
Samuel K. Lai, Ying-Ying Wang, Justin Hanes. Mucus-penetrating nanoparticles for drug and gene delivery to mucosal tissue. Advanced Drug Delivery Reviews 61 (2009) 158-171.
Shanyi Chen, William Samuel, Robert N. Fariss, Todd Duncan, R. Krishnan Kutty and Barbara Wiggert. Differentiation of human retinal pigment epithelial cells into neuronal phenotype by N-(4-hydroxyphenyl)retinamide. J of Neurochemistry, 84: 972-981, 2003.
Shumway BS, Kresty LA, Larsen PE, Zwick JC, Lu B, Fields HE, Mumper RJ, Stoner GD, Mallery SR. Effects of a topically applied bioadhesive berry gel on loss of heterozygosity indices in premalignant oral lesions.Clin Cancer Res ,14: 2421-2430.
Sietske T. Bakker, Johan P. de Winter and Hein te Riele. Learning from a paradox: recent insights into Fanconi anaemia through studying mouse models. Disease Models & Mechanisms. 2013, 6: 40-47.
Sokolovskaya, E., Rahmani, S., Misra, A. C., & Lahann, J. Dual-stimuli-responsive microparticles. ACS Appl. Mater. Interfaces 7, 9744-9751 (2015).
Soldin OP, Mattison DR. Sex Differences in Pharmacokinetics and Pharmacodynamics. Clin Pharmacokinet. 2009, 48: 143-157.
Spardy N, Duensing A, Charles D, Haines N, Nakahara T et al. The human papillomavirus type 16 E7 oncoprotein activates the Fanconi anemia (FA) pathway and causes accelerated chromosomal instability in FA cells. J Virol 2007, 81: 13265-13270.
Susan R. Mallery, Meng Tong, Brian S. Shumway, Alice E. Curran, Peter E. Larsen, Gregory M. Ness, Kelly S. Kennedy, George H. Blakey, George M. Kushner, Aaron M. Vickers, Brian Han, Ping Pei, and Gary D. Stoner. Topical Application of a Mucoadhesive Freeze-Dried Black Raspberry Gel Induces Clinical and Histologic Regression and Reduces Loss of Heterozygosity Events in Premalignant Oral Intraepithelial Lesions: Results from a Multicentered, Placebo-Controlled Clinical Trial. Clin Cancer Res 2014, 20: 1910-1924.
Susan R. Mallery, et al., Benefits of Multifaceted Chemopreventives in the Suppression of the Oral Squamous Cell Carcinoma (OSCC) Tumorigenic Phenotype, 2017, Cancer Prevention Research, 76-88.
Susan R. Mallery, Deric E. Budendorf, Matthew P. Larsen, Ping Pei, Meng Tong, Andrew S. Holpuch, Peter E. Larsen, Gary D. Stoner, Henry W. Fields, Kenneth K. Chan, Yonghua Ling, and Zhongfa Liu. Effects of Human Oral Mucosal Tissue, Saliva, and Oral Microflora on Intraoral Metabolism and Bioactivation of Black Raspberry Anthocyanins. Cancer Prey Res 2011, 4: 1209-1221.
Susan R. Mallery, Meng Tong, Gregory C. Michaels, Amber R. Kiyani, Stephen S. Hecht. Clinical and Biochemical Studies Support Smokeless Tobacco's Carcinogenic Potential in the Human Oral Cavity. Cancer Prev Res. 7: 23-32, 2014. http://cancerpreventionresearch.aacrjournals.org/content/7/1/23.full.
Taniguchi T, Garcia-Higuera I, Andreassen PR, Gregory RC, Grompe M, D'Andrea AD. S-phase-specific interaction of the Fanconi anemia protein, FANCD2, with BRCA1 and RAD51. Blood 2002,100: 2414-20.
Tong, M.; Han, B. B.; Holpuch, A. S.; Pei, P.; He, L.; Mallery, S. R. Inherent phenotypic plasticity facilitates progression of head and neck cancer: Endotheliod characteristics enable angiogenesis and invasion. Exp. Cell Res. 2013, 319, 1028-1042.
Velleur E and Deitrich R. Fanconi Anemia: young patients at high risk for squamous cell carcinoma. Mol Cell Ped 2014; 1: 9.
William,W.N.Jr et al., High-dose fenretinide in oral leukoplakia. Cancer Prev. Res. 2009 (Phila), 2, 22-26.
Xiao Wu, Kas Mucoadhesive Fenretinide Patches for Site-Specific Chemoprevention of Oral Cancer: Enhancement of Oral Mucosal Permeation of Fenretinide by Coincorporation of Propylene Glycol and Menthol. Mol Pharmaceutics. 2012 9: 937-945.
Yoon, J.; Lee, K.J.; Lahann, J. Multifunctional Polymer Particles with Distinct Compartments. J. Mat. Chem. 2011, 21, 8502.
International Preliminary Report on Patentability issued for Application No. PCT/US2018/022877, dated Sep. 26, 2019.
Cone, Richard A., "Mucus." In: *Mucosal Immunology, Third Edition* (ed. Mestecky, Jiri et al.), Academic Press, San Diego, pp. 49-72 (2005).
Extended European Search Report regarding European Patent Application No. 18767010.4, dated Dec. 10, 2020.

* cited by examiner

BIPHASIC | TRIPHASIC: SIDE-BY-SIDE | TRIPHASIC: PIE-SHAPED | TETRAPHASIC

ONE-PATCH SYSTEM | TWO-PATCH SYSTEM | 3D VIEW    EQUATORIAL VIEW
THREE-PATCH SYSTEM

CONTROLLED RELEASE pH DEPENDENT RELEASE

Patient 5 (600x) – Neg. Control

Patient 5 (600x)

Patient 7 (600x) – MRP1

Patient 7 (600x) – BCRP

NANOPARTICLES FOR DELIVERY OF CHEMOPREVENTIVE AGENTS

CROSS REFERENCE TO RELATED APPLICATIONS

This application is a national stage application filed under 35 U.S.C. § 371 of PCT/US2018/022877 filed Mar. 16, 2018, which claims the benefit of U.S. Provisional Patent Application Ser. No. 62/473,015 filed Mar. 17, 2017, and of U.S. Provisional Patent Application Ser. No. 62/575,683 filed Oct. 23, 2017, the disclosures of which are expressly incorporated herein by reference.

FIELD

The invention generally relates to nanoparticles, particularly Janus particles, capable of delivering chemopreventive agents to a subject.

BACKGROUND

Oral cancer represents a highly challenging clinical problem that dramatically impacts the lives of many patients (estimated 49,670 new oropharyngeal cancer cases and 9,700 deaths in U.S. during 2017). Unfortunately, oral squamous cell carcinoma (OSCC) is one of the most challenging-to-treat human cancers. These issues reflect the insidious nature of its early disease, reliance upon surgery as the primary treatment modality, and the difficulty of achieving loco-regional disease control. Over 35% of OSCC patients die from massive local recurrence and despite enhanced protocols such as inductive chemotherapy and radiation intensification programs, non-HPV-related OSCC survival rates remain among the lowest for solid tumors. Further, even OSCC patients who are cured by surgery must face major esthetic and functional changes of their face and mouth. Similar to other carcinomas, OSCCs arise from malignant progression of its precursor lesion i.e. oral intraepithelial neoplasia (OIN). While not all OIN lesions transform, ~85% of high risk lesions (severe dysplasia and carcinoma-in-situ) progress to oral squamous cell carcinoma.

In addition, approximately 30% OIN lesions recur despite microscopically-confirmed complete excision. Consequently, patients with OIN require multiple biopsies and live with the fear that they will develop oral cancer. Also, OSCC clinical care costs are among the highest of all cancers which results in a significant socio-economic burden. Clearly, identification of effective chemopreventive strategies to prevent OIN progression to OSCC emerges as an innovative approach to address this pressing and unmet clinical need.

Tobacco and alcohol use and more recently oncogenic human papilloma viruses are the best recognized risk factors for the development of OSCC. There are also a group of diseases characterized by defective DNA repair [for example, Fanconi Anemia (FA)] in which patients have a much higher incidence (500 to 700-fold) of developing OSCC.

Regardless of etiology, OSCC remains a worldwide health problem for afflicted patients. Five-year survival rates for all persons remain around 57%; one of the lowest for all solid tumors. As radical surgery is the primary OSCC treatment modality, even persons cured by surgery endure loss of facial and jaw structures vital for speech, eating and aesthetics. For persons with FA these concerns are magnified. FA patients face markedly greater risks with an abysmal prognosis (e.g. death within two years of diagnosis). Development of effective, well-tolerated OSCC chemoprevention is essential for this patient cohort.

Standard OSCC chemoprevention trials used systemic administration (usually pills) of a single agent. This approach has major deficits including deleterious side effects, inability to achieve adequate levels at the treatment site, and lack of efficacy. Development of new, efficacious chemopreventive agents which reduce local and systemic side effects and increase local agent concentrations at desired sites would represent a significant advancement in the treatment of FA specifically and OSCC generally.

The compositions and methods disclosed herein address these and other needs.

SUMMARY

Disclosed herein are nanoparticle compositions and methods of use such as for chemoprevention of cancer, for example oral squamous cell carcinoma (OSCC). The nanoparticle composition comprises a Janus particle comprising at least two chemopreventive agents, wherein at least one of the chemopreventive agents is selected from freeze-dried black raspberries (BRB), a synthetic vitamin A analogue, N-acetylcysteine (NAC), and an anti-interleukin 6 agent. Methods for improving oral health comprising administering to a subject the nanoparticle compositions herein are also disclosed. Oral administration of the nanoparticle compositions can provide local delivery of chemopreventive agents while minimizing adverse systemic effects.

In one aspect, disclosed herein are nanoparticle compositions comprising: a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent. In some embodiments, the at least two chemopreventive agents selected are BRB and fenretinide (4-HPR), 4-HPR and NAC, 4-HPR and tocilizumab, or NAC and tocilizumab. In some embodiments, the composition further comprises a mucoadhesive or a mucous penetration enhancer. In some embodiments, the nanoparticle comprises at least 10 weight percent of a first chemopreventive agent and at least 10 weight percent of a second chemopreventive agent. In some embodiments, the nanoparticle composition is formulated for oral delivery, for example in an oral rinse, troche, topical gel, or mucoadhesive patch formulation.

In a further aspect of the invention, provided herein is a method of chemoprevention comprising: administering to a subject a nanoparticle composition in an amount sufficient to prevent the recurrence of a cancer, wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In another aspect, disclosed herein is a method of chemoprevention comprising: administering to a subject a nanoparticle composition in an amount sufficient to inhibit the progression of a precancerous lesion to a cancer, wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In one embodiment, the cancer is oral squamous cell carcinoma (OSCC).

In another aspect, provided herein are methods for improving oral health comprising: administering to a subject a nanoparticle composition comprising a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent. In some embodiments, the at least two chemopreventive agents selected are BRB and fenretinide (4-HPR), 4-HPR and NAC, 4-HPR and tocilizumab, or NAC and tocilizumab. In some embodiments, the nanoparticle composition is administered as a chemopreventive for periodontal disease. In some embodiments, the nanoparticle composition is administered locally to the oral epithelia (by, e.g., an oral rinse, troche, topical gel, or mucoadhesive patch formulation).

BRIEF DESCRIPTION OF THE DRAWINGS

The accompanying figures, which are incorporated in and constitute a part of this specification, illustrate several aspects described below.

FIG. 1A) Schematic of electrohydrodynamic co-jetting. FIG. 1B) Fluorescence micrographs of nanoparticles containing two or more fluorescent compounds. FIG. 1C) Fluorescence micrographs of nanoparticles and comparison of singular or multiple patch systems. FIG. 1D) Micrographs of Janus particles in the nm and μm range. FIG. 1E) Graphs depicting chemopreventive release from nanoparticles over time.

FIG. 4A) Schematic showing bicompartmental design used in the electrohydrodynamic co-jetting procedure. FIG. 4B) Schematic showing an example nanoparticle with encapsulated chemopreventive agents/chemotherapeutics and surface exposed molecules. FIG. 4C) Schematic showing strategy for conjugating molecules via UV-induced thiol-alkyne reaction. FIG. 4D) Schematic showing example nanoparticle formulations. i) nanoparticle containing two surface chemistries but only one chemopreventive; ii) nanoparticle containing surface-bound molecules (e.g., targeting molecules); iii) nanoparticle containing two surface chemistries and chemopreventives bound by both chemistries.

FIG. 5C and FIG. 5D (immunohistochemical stains for two Phase III drug egress enzymes MRP1 and BCRP) demonstrate intraepithelial nanoparticle retention despite the presence of these Phase III enzymes.

FIG. 6A, FIG. 6C, FIG. 6E and FIG. 6G depict negative controls (cells not treated with nanoparticles). FIG. 6B, FIG. 6D, and FIG. 6F show fluorescent nanoparticle internalization images (green), cellular nuclei are blue. FIG. 6H shows an immunocytochemistry study to confirm nanoparticle size consistency using both fluorescent and immunocytochemistry.

FIG. 8A shows the invasiveness of 3 validated oral keratinocyte cell lines was determined in the presence of: no treatment, BRB separately, 4-HPR separately and a BRB+4-HPR treatment combination. Greater purple intensity depicts higher cell invasiveness. FIG. 8B depicts a qualitative assessment of basement membrane invasion relative to cell line matched control cells. n=8, mean±s.e.m. *=p<0.0001, one-way ANOVA with a Bonferroni multiple comparisons post hoc test.

DETAILED DESCRIPTION

Figure 1A:
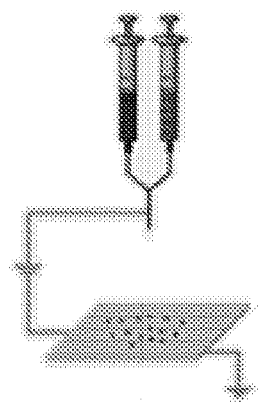
FIGS. 1A-1E depict the construction and properties of Janus particles co-jetted with two or more molecules.

Disclosed herein are novel Janus nanoparticle compositions that locally deliver pharmacologically relevant levels of chemopreventive agents to the site of administration. The nanoparticle compositions can provide on-demand chemopreventive agents, wherein at least one of the chemopreventive agents is selected from freeze-dried black raspberries (BRB), a synthetic vitamin A analogue, N-acetylcysteine (NAC), and an anti-interleukin 6 agent. In some embodiments, the nanoparticles can be targeted to one or more tissues or cell types. Local oral delivery of the nanoparticle compositions can provide therapeutically relevant local levels of chemopreventive agents while minimizing adverse systemic effects. These novel controlled-release nanoparticle compositions and methods are also disclosed herein to improve oral health.

Reference will now be made in detail to the embodiments of the invention, examples of which are illustrated in the drawings and the examples. The present disclosure may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used herein, "administration" of an agent to a subject includes any route of introducing or delivering to a subject an agent to perform the agent's intended function(s). Administration can be carried out by any suitable route, including orally, intranasally, parenterally (intravenously, intramuscularly, intraperitoneally, or subcutaneously), topically, and the like. "Systemic administration" refers to the introducing or delivering to a subject an agent via a route which introduces or delivers the agent to extensive areas of the subject's body (e.g. greater than 50% of the body), for example through entrance into the circulatory, gastrointestinal, or lymphatic systems. By contrast, "local administration" refers to the introducing or delivery to a subject an agent via a route which introduces or delivers the agent to the area or areas within the local vicinity of the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

As used herein, the term "chemopreventive" and "chemopreventive agent" are used interchangeably and refer to any chemical or composition comprising one or more chemicals that, when administered to a subject, prevents a disease or disorder (e.g. cancer) from progressing or recurring. A chemopreventive agent can slow, block, suppress, or reverse the effects of cancer causing factors or symptoms thereof. Chemopreventive agents may interfere with initiation, promotion, progression, or all stages of multistage carcinogenesis. The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the term "chemopreventive" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

As used herein, the term "preventing" a disorder or unwanted physiological event in a subject refers specifically to the prevention of the progression or recurrence of symptoms and/or their underlying cause, wherein the subject may or may not exhibit heightened susceptibility to the disorder or event (for example, either inducing regression or preventing progression). As used herein, "preventing oral cancer" includes inducing regression of precancerous lesions, preventing or delaying the progression of premalignant surface oral epithelial lesions or recurrence of previously treated oral cancer (for example, oral squamous cell carcinoma) or signs or symptoms thereof.

The term "effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts.

An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, the term "pharmaceutically acceptable" component can refer to a component that is not biologically or otherwise undesirable, e.g., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

As used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "controlled release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

Nanoparticles Comprising Chemopreventive Agents

In one aspect, disclosed herein are nanoparticle compositions comprising: a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

Modern medicine has increasingly recognized the value of nanoparticle systems and materials for an array of applications, for example, in agent delivery, imaging, biosensing, and other uses. In the last two decades, a number of nanoparticle-based therapeutic and diagnostic agents have been developed for the treatment of cancer, diabetes, pain, asthma, allergy, and infections. These nanoscale agents can provide more effective and/or more convenient routes of administration, lower therapeutic toxicity, extend the product life cycle, and ultimately reduce health-care costs. Local delivery of nanoparticles comprising chemopreventive agents, as compared to systemic delivery of an agent, has the potential to permit use of appreciably lower levels (for example, >1,000 fold less) of the agent while providing therapeutic target levels and eliminating deleterious side effects.

The compositions disclosed herein comprise nanoparticles, particularly Janus particles. The term "Janus particles", as used herein, refers to particles having two or more spatially oriented chemistries. The different chemistries are attributed to distinct compartments (e.g. hemispheres) with differences in composition, polarity, hydrophobicity, or other chemical or physical properties in each compartment (see FIG. 1B-C). For example, a Janus particle may contain a hydrophobic surface and a hydrophilic surface, or alternatively or in combination, separate surfaces having chemistries capable of binding separate ligands. Thus, Janus particles are suitable for stabilization and delivery of two or more chemically distinct compounds. In some embodiments, Janus particles have been optimized for size and composition to facilitate epithelial cell internalization and to regulate compound release.

In some embodiments, the nanoparticle may be a multiphasic nanoparticle that comprises multiple compositionally distinct compartments. Each compartment may thus comprise distinct material compositions. Multiphasic nanoparticles may have a variety of shapes and may comprise two, three, or more distinct compartments. Such multiphasic nano-components may be formed by electrified jetting of materials that comprise one or more polymers, such as that disclosed in U.S. Pat. Nos. 7,767,017; 7,947,772; 8,043,480; and 8,187,708; which are incorporated by reference in their entirety.

Janus particle size and composition optimization can facilitate epithelial cell internalization and regulate compound release (permitting, for example, controlled release of agents). Janus particles may be made of FDA-approved components frequently used for food additives, thereby minimizing safety concerns. In addition, Janus nanoparticles can be optimized to enable retention in the intracellular space, commonly called the extracellular matrix.

A wide array of materials can be used to form Janus particles and other nanoparticles. The compositional parameters of the herein disclosed nanoparticles (e.g. Janus particles) are limited primarily by in vivo toxicity issues and compatibility with the molecules and materials to be attached to the particles. For example, Janus particles can be formed from polymeric materials (e.g. polystyrene, polymethylacrylate, polybutadiene), metals and metal oxides (e.g. gold, manganese oxide, zinc oxide), crystalline materials such as silicon oxides, other materials, and mixtures thereof. Methods to form Janus particles include coating, microcontact printing, microfluidic separation of organic phase components, electrohydrodynamic co-jetting, self-assembly of block copolymers, competitive adsorption, etc.

In some embodiments, the Janus particle comprises poly (lactic-co-glycolic acid) (PLGA). Janus particles comprised of FDA-approved PLGA are frequently used for food additives. Hence, use of Janus particles comprised of PLGA in oral treatment compositions have minimal product safety concerns. Further, PLGA is biodegradable, which can facilitate release of components attached to or encapsulated within the nanoparticle. In other formulations, nanoparticles can be comprised of chitosan. Chitosan is fully biodegradable and biocompatible.

As the name suggests, "nanoparticles" such as Janus particles have sizes ranging in the nanometer scale. However, many modified nanoparticles have wider ranges of sizes (see e.g., FIG. 1D). For simplicity, the terms "nanoparticle" and "Janus particle" as used herein refer to particles having sizes in the nanometer and/or micrometer range. In some embodiments, the nanoparticles may have a diameter of at least about 1 nm, 10 nm, 50 nm, 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 4000 nm, 5000 nm, 6000 nm, 7000 nm, 8000 nm, or at least 9000 nm. In some embodiments, the nanoparticles may have a diameter of less than 10,000 nm, 9000 nm, 8000 nm, 7000 nm, 6000 nm, 5000 nm, 4500 nm, 4000 nm, 3500 nm, 3000 nm, 2500 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 250 nm, or less than 100 nm.

Figure 2:
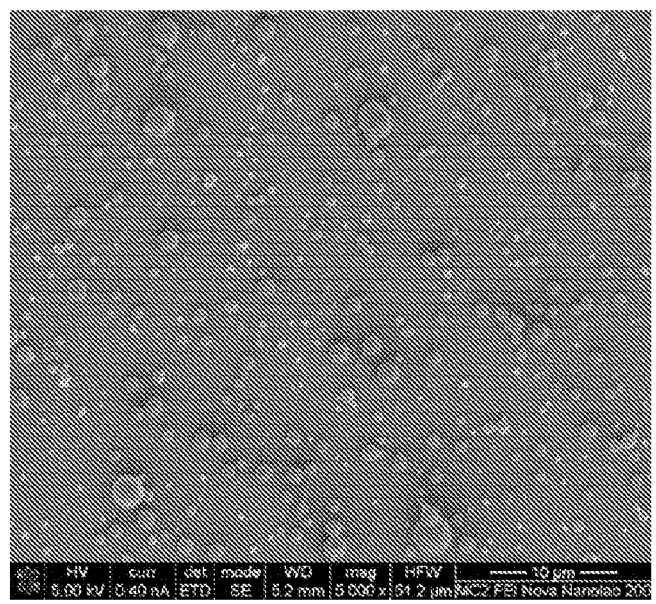
FIG. 2 is a micrograph of Janus particles co-loaded with freeze-dried black raspberries (BRB) and fenretinide (4-HPR).

The diameter of nanoparticles can range from any of the minimum values described above to any of the maximum values described above, for example from 1 nm to 10,000 nm, 50 nm to 5,000 nm, 100 nm to 2500 nm, 200 nm to 2000 nm, or 500 nm to 1000 nm. As an example, FIG. 2 is a micrograph showing BRB and 4-HPR co-loaded Janus particles ranging in diameter from 100 nM to 5 µM. This list is intended to be merely for purposes of example only, and any of numerous combinations of minimum and maximum values described above may be used as a range of nanoparticle diameters in a vehicle.

Production of Janus particles can result in bimodal or multi-modal distributions of diameters. Desired diameter ranges (e.g. a monodispersed diameter range) can be separated by centrifugation and collected. Monodispersed diameter ranges can be analyzed and counted using several methods including, for example, dynamic light scattering and nanoparticle tracking analysis. In some embodiments, the nanoparticles have a monodispersed average diameter distribution. In some embodiments, the nanoparticles have a monodispersed average diameter of about 1 nm, 10 nm, 50 nm, 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 4000 nm, 5000 nm, 6000 nm, 7000 nm, 8000 nm, 9000 nm, or 10,000 nm. As used herein, a monodispersed average diameter distribution refers to a population of nanoparticles wherein greater than 80 percent of the population vary in diameter by about 20 percent or less from the average diameter. Optionally, the parameters for a monodispersed average diameter distribution can be made more stringent (e.g. greater than 85, 90, or 95 percent of the population vary in diameter by about 15, 10, or 5 percent or less from the average diameter, wherein any combination of percentages of the population can be combined with any percent variations in diameter).

In some embodiments, the at least two chemopreventive agents comprise freeze-dried black raspberries (BRB). BRB can be obtained by freeze drying black raspberries (and is available from, for example, Berrihealth, Corvallis, Oreg.). Several effective freeze-drying agents and methods include sublimation, vacuum-mediated temperature reduction, dry ice (solidified carbon dioxide) exposure, among other methods. Freeze-dried black raspberries may be further formed into a powder by, for example, pulverization. In some embodiments, the black raspberries are *Rubus occidentalis*.

BRB is a chemopreventive which can be included in the artificial nanoparticles. Thus, the at least two chemopreventive agents can comprise a chemopreventive including, but not limited to limonin, Ocimum sanctum, tumeric curcumins, green tea polyphenols, mint, fruit and/or vegetable extracts, tea leaf flavanoid extracts, and combinations thereof.

BRB contains redox scavenging molecules which suppress oxidative signaling and reactive oxidant mediated DNA damage. BRB inhibits NF-κB signaling and can induce beneficial keratinocyte growth state modulation in human oral intraepithelial neoplasia (OIN) lesions. While BRB contains numerous active components including phenolic phytochemicals e.g. anthocyanins and coumaric and ferulic acids, anthocyanins deliver the greatest chemopreventive impact. BRB contain four anthocyanins: cyanidin-3-rutinioside cyanidin-3-glucoside, cyanidin-3-xylosylrutinoside, and cyanidin-3-sambuside (see FIG. 3). In some embodiments, isolated anthocyanins may substitute for BRB as a chemopreventive agent. For example, in some embodiments, nanoparticles can comprise an estimated dosage of 2-10 μmol/L cyanidin rutinoside as a first chemopreventive of the at least two chemopreventive agents. BRB is generally safe for human consumption.

In some embodiments, the at least two chemopreventive agents comprise a synthetic vitamin A analogue. In some embodiments, the synthetic vitamin A analogue is fenretinide (4-HPR). It is well known that 4-HPR can induce apoptosis and/or terminal differentiation. 4-HPR patches increase oral keratinocyte terminal differentiation and protective Phase II enzyme levels in vivo. Further, 4-HPR inhibits proteins integral for OSCC gratuitous signaling and cell invasion e.g. FAK, Pyk2 and STAT3. Notably, gratuitous activation of these tyrosine kinases and basement membrane invasion enables transformation of premalignant epithelial lesions to OSCC. Human surface oral epithelia possess 4-HPR bioactivating and glucuronidating enzymes, while previous experiments did not detect 4-HPR inactivating enzymes in the tissue sections from multiple human donors. Furthermore, local delivery formulations eliminate the bioavailability and inactivation issues that were encountered with systemic 4-HPR delivery.

In some embodiments, the at least two chemopreventive agents comprise a thiol-sparing agent. One non-limiting example of a thiol-sparing agent is N-acetylcysteine (NAC). NAC exhibits electrophile scavenging capacity, which modulates damage due to alkylating agents. NAC also functions as a glutathione precursor, thereby augmenting GSH levels and GSH-s-transferase and GSH peroxidase function. Oral tablet and injectable NAC formulations are FDA approved for acetaminophen overdose.

In some embodiments, the at least two chemopreventive agents comprise a biologic. In some embodiments, the at least two chemopreventive agents comprise an anti-interleukin 6 (also referred to as anti-IL-6 or anti-IL6) agent. IL-6 is an integral cancer-promoting cytokine due to its proinflammatory, proangiogenic and proproliferative effects. OSCC cells release high levels of IL-6 and secrete sIL-6R, which are both targets and effectors of this multifaceted cytokine. One example of a suitable biologic is Tocilizumab (Actemra®), which is a humanized anti-IL6R monoclonal antibody approved by the US FDA for treatment of several forms of arthritis. Tocilizumab significantly reduces growth of established OSCC tumor explants. An additional FDA-approved antibody is situximab (Sylvant®). Additional anti-interleukin-6 agents include, but are not limited to, sarilumab, olokizumab, elsilimomab, BMS-945429, sirukumab, and CPSI-2364. Initiation of the angiogenic switch and increased tumor-associated angiogenesis are important aspects for the progression of premalignant disease to overt OSCC and continuation of OSCC tumor growth, respectively.

Numerous other compounds, for example 2-methoxyestradiol, are naturally occurring angiogenic inhibitors. In some embodiments, 2-methoxyestradiol is administered in combination with at least one of the chemopreventive agents selected from the group consisting of freeze-dried black raspberries (BRB), a synthetic vitamin A analogue, N-acetylcysteine (NAC), and an anti-interleukin 6 agent.

In some embodiments, the anti-IL-6 agent is an IL-6 receptor inhibitor. In some embodiments, the anti-IL-6 agent is an anti-IL-6 receptor antibody. In some embodiments, the anti-IL-6 receptor antibody/antagonist is tocilizumab.

For optimal efficacy, tocilizumab should be localized at the interstitial space between keratinocytes in proximity to the IL-6 generating inflammatory and OSCC cells. This arrangement for tocilizumab helps to suppress proproliferative, proinflammatory IL-6 signaling. Thus, nanoparticles which expose tocilizumab to the interstitial space are particularly advantageous. In some embodiments, nanoparticles can be reversibly bound with tocilizumab, such that the nanoparticles locally release free tocilizumab in the interstitial space. Reversibly bound tocilizumab can optionally be entrapped within the nanoparticle polymer matrix. In some embodiments, tocilizumab can be covalently bound to the nanoparticle surface, such that the nanoparticles locally present bound tocilizumab in the interstitial space.

Patents and patent publications related to anti-IL-6R antibodies include, for example: U.S. Pat. No. 5,171,840 (Kishimoto), U.S. Pat. No. 5,480,796 (Kishimoto), U.S. Pat. No. 5,670,373 (Kishimoto), U.S. Pat. No. 5,851,793 (Kishimoto), U.S. Pat. No. 5,990,282 (Kishimoto), U.S. Pat. No. 6,410,691 (Kishimoto), U.S. Pat. No. 6,428,979 (Kishimoto), U.S. Pat. No. 5,795,965 (Tsuchiya et al.), U.S. Pat. No. 5,817,790 (Tsuchiya et al.), U.S. Pat. No. 7,479,543 (Tsuchiya et al.), US 2005/0142635 (Tsuchiya et al.), U.S. Pat. No. 5,888,510 (Kishimoto et al.), US 2001/0001663 (Kishimoto et al.), US 2007/0036785 (Kishimoto et al.), U.S. Pat. No. 6,086,874 (Yoshida et al.), U.S. Pat. No. 6,261,560 (Tsujinaka et al.), U.S. Pat. No. 6,692,742 (Nakamura et al.), U.S. Pat. No. 7,566,453 (Nakamura et al.), U.S. Pat. No. 7,771,723 (Nakamura et al.), US 2002/0131967 (Nakamura et al.), US 2004/0247621 (Nakamura et al.), US 2002/0187150 (Mihara et al.), US 2005/0238644 (Mihara et al.), US 2009/0022719 (Mihara et al.), US 2006/0134113 (Mihara), U.S. Pat. No. 6,723,319 (Ito et al.), U.S. Pat. No. 7,824,674 (Ito et al.), US 2004/0071706 (Ito et al.), U.S. Pat. No. 6,537,782 (Shibuya et al.), U.S. Pat. No. 6,962,812 (Shibuya et al.), WO 00/10607 (Akihiro et al.), US 2003/0190316 (Kakuta et al.), US 2003/0096372 (Shibuya et al.), U.S. Pat. No. 7,320,792 (Ito et al.), US 2008/0124325 (Ito et al.), US 2004/0028681 (Ito et al.), US 2008/0124325 (Ito et al.), US 2006/0292147 (Yoshizaki et al.), US 2007/0243189 (Yoshizaki et al.), US 2004/0115197 (Yoshizaki et al.), US 2007/0148169 (Yoshizaki et al.), U.S. Pat. No. 7,332,289 (Takeda et al.), U.S. Pat. No. 7,927,815 (Takeda et al.), U.S. Pat. No. 7,955,598 (Yoshizaki et al.), US 2004/0138424 (Takeda et al.), US 2008/0255342 (Takeda et al.), US 2005/0118163 (Mizushima et al.), US 2005/0214278 (Kakuta et al.), US 2008/0306247 (Mizushima et al.), US 2009/0131639 (Kakuta et al.), US 2006/0142549 (Takeda et al.), U.S. Pat. No. 7,521,052 (Okuda et al.), US 2009/0181029 (Okuda et al.), US 2006/0251653 (Okuda et al.), US 2009/0181029 (Okuda et al.), US 2007/0134242 (Nishimoto et al.), US 2008/0274106 (Nishimoto et al.), US 2007/0098714 (Nishimoto et al.), US 2010/0247523 (Kano et al.), US 2006/0165696 (Okano et al.), US 2008/0124761 (Goto et al.), US 2009/0220499 (Yasunami), US 2009/0220500 (Kobara), US 2009/0263384 (Okada et al.), US 2009/0291076 (Morichika et al.), US 2009/0269335 (Nakashima et al.), US 2010/0034811 (Ishida), US 2010/0008907 (Nishimoto et al.), US 2010/0061986 (Takahashi et al.), US 2010/0129355 (Ohguro et al.), US 2010/0255007 (Mihara et al.), US 2010/0304400 (Stubenrach et al.), US 2010/0285011 (Imaeda et al.), US 2011/0150869 (Mitsunaga et al.), WO 2011/013786 (Maeda) and US 2011/0117087 (Franze et al.).

Standard OSCC chemoprevention trials used systemic administration (usually pills) of a single agent. This approach has major deficits including deleterious side effects, inadequate agent levels at the treatment site, and lack of efficacy. However, local delivery approaches allow for use of appreciably lower agent levels (for example, >1,000 fold less) while providing therapeutic target levels and reducing/eliminating deleterious side effects. Early nanoparticle-agent delivery systems permitted such local delivery of single agents. However, combinatorial use of chemopreventive agents can provide therapeutic advantages beyond either agent alone.

The nanoparticles can comprise at least two chemopreventive agents. However, the nanoparticles are not limited to two chemopreventive agents, and in some embodiments, the nanoparticles comprise more than two chemopreventive agents. In some embodiments, the nanoparticles comprise three or more chemopreventive agents. In some embodiments, the nanoparticles comprise four or more chemopreventive agents. Notably, patient responsiveness to a chemopreventive compound is heterogenous. As such, the combined use of two or more chemopreventive agents which are locally delivered in nanoparticles to avoid or reduce deleterious systemic effects facilitates increased personalization in approaches to OSCC cancer chemoprevention.

In some embodiments, the at least two chemopreventive agents have additive chemopreventive effects against periodontal disease and/or OSCC recurrence or progression. In some embodiments, the at least two chemopreventive agents have synergistic chemopreventive effects against periodontal disease and/or OSCC recurrence or progression.

In some embodiments, the chemopreventive agents selected are BRB and 4-HPR. In some embodiments, chemopreventive agents selected are 4-HPR and NAC. In some embodiments, the chemopreventive agents selected are 4-HPR and tocilizumab. In some embodiments, the chemopreventive agents selected are NAC and tocilizumab. Nanoparticles may contain any combination of up to all four of the chemopreventive agents BRB, 4-HPR, NAC, and tocilizumab. Further, nanoparticles may include additional chemopreventive agents, antimicrobial agents, and/or other surface decorating molecules, as discussed herein.

The Janus particle comprises at least two chemopreventive agents. In addition to the at least one chemopreventive agent selected from the group consisting of freeze-dried black raspberries (BRB), a synthetic vitamin A analogue, N-acetylcysteine (NAC), and an anti-interleukin 6 agent, the Janus particle can comprise a wide array of one or more chemopreventive agents. Non-limiting examples of chemopreventive agents include anthocyanins, tamoxifen, raloxifene, non-steroidal anti-inflammatory drugs (NSAIDs), glutathione, glucosinolates, isothiocyanates, caretonoids (e.g., β-carotene), limonin, retinyl acetate, Ocimum sanctum, long chain polyunsaturated fatty acids, vitamin D, folate, vitamin E, protease inhibitors, vitamin A, retinoids, calcium, flavonoids, curcumins, quecetin, quercetin, sulforaphane, trans-pterostilbene, gemcitabine, paclitaxel, cisplatin, dasatinib, terpenes, organosulfur compounds (e.g., allyl methyl trisulfide, allyl methyl disulfide, diallyl trisulfide, diallyl sulfide), inositol hexaphosphate, epigallocatechin, 18-β-glycyrrhetinic acid, dithiolethiones, ellagic acid, pyranocoumarin, COX-2 inhibitors, ONYX-015, tyrosine kinase inhibitors, angiogenesis inhibitors, selenium, folic acid, polyphenols (e.g., green tea polyphenols), statins, metformin, resveratrol, mint, and combinations thereof.

In some embodiments, the chemopreventive agent is effective against cancer stem cells. In some embodiments, the chemopreventive agent targets a molecule overproduced by cancer stem cells. In some embodiments, the chemopreventive agent comprises an aldehyde dehydrogenase inhibitor. In some embodiments, the chemopreventive agent comprises disulfiram (Antabuse). Cancer stem cells are primarily responsible for OSCC recurrence and, as such, chemoprevention of recurrence (e.g., tertiary chemoprevention) benefits from inclusion of chemopreventives which are effective against cancer stem cells. Disulfiram is a FDA approved drug currently administered to prevent use of alcohol by recovering alcoholics. Due to cancer stem cells unique biochemistry, aldehyde dehydrogenase is markedly overexpressed and its activity helps to convey cancer stem cells with a growth advantage. Thus, disulfiram has the capability to target cancer stem cells.

In some embodiments, the nanoparticles further comprise one or more targeting agents. As used herein, a "targeting agent" is a molecule or composition comprising more than one molecule which facilitates delivery of the nanoparticles to one or more tissue types or cell types. As a nonlimiting example, a targeting agent can be an antibody which binds a receptor present in the tissue types or cell types. As another nonlimiting example, the targeting agent can be a molecule which is chemically altered in the environment of the tissue types or cell types, for example a molecule which degrades in hypoxic or acidic conditions of tumor microenvironments. In some embodiments, the targeting agent targets cancer cells or tumor cells. In some embodiments, the targeting agent targets OSCC. In some embodiments, the targeting agent targets cancer stem cells. In some embodiments, the targeting agent promotes cellular attachment. In some embodiments, the targeting agent comprises the triamino acid sequence, arginine-glycine-aspartate, also called RGD peptide.

Nanoparticles of the present invention can include antimicrobial agents. Nanoparticles may contain one or more antimicrobial agents in combination with two or more chemopreventive agents. Examples of suitable antimicrobial agents include, for example, acetoxycycloheximide, aciduliprofundum, actaplanin, actinorhodin, alazopeptin, albomycin, allicin, allistatin, allyl isothiocyanate, ambazone, aminocoumarin, aminoglycosides, 4-aminosalicylic acid, ampicillin, ansamycin, anthramycin, antimycin A, aphidicolin, aplasmomycin, archaeocin, arenicin, arsphenamine, arylomycin A2, ascofuranone, aspergillic acid, avenanthramide, avibactam, azelaic acid, bafilomycin, bambermycin, beauvericin, benzoyl peroxide, blasticidin S, bottromycin, brilacidin, caprazamycin, carbomycin, cathelicidin, cephalosporins, ceragenin, chartreusin, chromomycin A3, citromycin, clindamycin, clofazimine, clofoctol, clorobiocin, coprinol, coumermycin A1, cyclic lipopeptides, cycloheximide, cycloserine, dalfopristin, dapsone, daptomycin, debromomarinone, 17-dimethyl aminoethylamino-17-demethoxygeldanamycin, echinomycin, endiandric acid C, enediyne, enviomycin, eravacycline, erythromycin, esperamicin, etamycin, ethambutol, ethionamide, (6S)-6-fluoroshikimic acid, fosfomycin, fosmidomycin, friulimicin, furazolidone, furonazide, fusidic acid, geldanamycin, gentamycin, gepotidacin, glycyciclines, glycyrrhizol, gramicidin S, guanacastepene A, hachimycin, halocyamine, hedamycin, helquinoline, herbimycin, hexamethylenetetramine, hitachimycin, hydramacin-1, isoniazid, kanamycin, katanosin, kedarcidin, kendomycin, kettapeptin, kidamycin, lactivicin, lactocillin, landomycin, landomycinone, lasalocid, lenapenem, leptomycin, lincosamides, linopristin, lipiarmycins, macbecin, macrolides, macromomycin B, maduropeptin, mannopeptimycin glycopeptide, marinone, meclocycline, melafix, methylenomycin A, methylenomycin B, monensin, moromycin, mupirocin, mycosubtilin, myriocin, myxopyronin, naphthomycin A, narasin, neocarzinostatin, neopluramycin, neosalvarsan, neothramycin, netropsin, nifuroxazide, nifurquinazol, nigericin, nitrofural, nitrofurantoin, nocathiacin I, novobiocin, omadacycline, oxacephem, oxazolidinones, penicillins, peptaibol, phytoalexin, plantazolicin, platensimycin, plectasin, pluramycin A, polymixins, polyoxins, pristinamycin, pristinamycin IA, promin, prothionamide, pulvinone, puromycin, pyocyanase, pyocyanin, pyrenocine, questiomycin A, quinolones, quinupristin, ramoplanin, raphanin, resistome, reuterin, rifazalil, rifamycins, ristocetin, roseophilin, salinomycin, salinosporamide A, saptomycin, saquayamycin, seraticin, sideromycin, sodium sulfacetamide, solasulfone, solithromycin, sparassol, spectinomycin, staurosporine, streptazolin, streptogramin, streptogramin B, streptolydigin, streptonigrin, styelin A, sulfonamides, surfactin, surotomycin, tachyplesin, taksta, tanespimycin, telavancin, tetracyclines, thioacetazone, thiocarlide, thiolutin, thiostrepton, tobramycin, tricsubjectatin A, triclosan, trimethoprim, trimethoprim, tunicamycin, tyrocidine, urauchimycin, validamycin, viridicatumtoxin B, vulgamycin, xanthomycin A, xibornol, and combinations thereof. In some embodiments, the antimicrobial agent comprises doxycycline, metronidazole, or combinations thereof.

Nanoparticle agent delivery systems provide advantages in controlled agent dosing. Nanoparticles comprising at least two chemopreventive agents can have controlled ratios of the two agents when the nanoparticles are administered to the target site. This is especially advantageous compared to systemic administration of two agents intended to have controlled ratios because the systemically administered agents may have different kinetics of circulation, uptake, and/or metabolism. In electrohydrodynamic co-jetting, agent concentrations in the jetting solution of each needle determine the ratio between the at least two chemopreventive agents in the resulting nanoparticles, and thus can be used to control the ratio delivered to the oral epithelia for synergistic effects. In some embodiments, the nanoparticle comprises at least two chemopreventive agents having a ratio of concentrations of about 1:1, 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3:1, 4:1, 5:1, 6:1, 7:1, 8:1, 9:1, 10:1, 20:1, 25:1, 30:1, 40:1, 50:1, 75:1, 100:1, 250:1, 500:1, 750:1, or 1,000:1, or greater than 1,000:1. In embodiments comprising nanoparticles comprising more than two chemopreventive agents (e.g. three chemopreventive agents), the above recited concentration ratios may apply to any two of the chemopreventive agents.

Electrohydrodynamic co-jetting is one particularly useful method of preparing the herein described nanoparticles. As discussed, electrohydrodynamic co-jetting involves minimal mixing of polymer solutions, thereby resulting in particles having compartmentalized binding chemistries. The number of compartmentalized binding chemistries per particle may reflect the number of chemopreventive agents to be combined with the nanoparticles. For example, a nanoparticle having two distinct binding chemistries may be expected to be loaded with two distinct agents. However, this is not a strict rule for nanoparticle formation, and such is not always the case. In some embodiments, a nanoparticle may have more distinct binding chemistries than loaded chemopreventive agents. For example, a triphasic nanoparticle (see FIG. 1B) having three distinct binding chemistries may be loaded with the chemopreventive agents BRB and 4-HPR. In such an embodiment, the third distinct binding chemistry can, for example, be used to load surface decoration molecules, as discussed herein. In some embodiments, a nanoparticle may be loaded with more chemopreventive agents than it has distinct binding chemistries. As an example, a monophasic nanoparticle having one surface chemistry may be loaded with both of the chemopreventive agents BRB and 4-HPR. In such an embodiment, the nanoparticle can be made homogenous by using a solvent in the electrohydrodynamic co-jetting spray which dissolves both agents. As an example, a nanoparticle can be loaded with both BRB and 4-HPR as a homogenous mixture when both chemopreventive agents are dissolved in dimethylformamide (DMF). In some embodiments, the chemopreventive agent is encapsulated in a nanoparticle. An encapsulated chemopreventive agent can be attached to a binding chemistry within the nanoparticle, or may be encapsulated without being attached to a binding chemistry. in some embodiments, a chemopreventive agent is encapsulated in one compartment (e.g., a first hemisphere) within the nanoparticle, and a second component (e.g., a second chemopreventive agent, an antimicrobial compound, a chemotherapeutic agent, etc., or combinations thereof) is encapsulated in a second compartment (e.g., a second hemisphere) within the nanoparticle. In some embodiments, the encapsulated components can be released in vivo by, for example, biodegradation of the nanoparticle. In some embodiments, the chemopreventive agent (e.g., an anti-interleukin 6 agent) is attached to the outer surface of the nanoparticle, for example by attachment to a binding chemistry on the surface of the nanoparticle.

Nanoparticles may be loaded with differing amounts of chemopreventive agents. In some embodiments, the nanoparticle can be loaded with at least 0.1, 0.5, 1, 2, 3, 4, 5, 6, 7, 8, 9, or 10 weight percent of a chemopreventive agent. In some embodiments, the nanoparticle can be loaded with at least 15, 20, 25, 30, 40, or 50 weight percent of a chemopreventive agent. One parameter which can be used to modify loading efficiency includes modifying the solvent in which the chemopreventive agent is dissolved. For instance, 4-HPR loading can be adjusted by use of a solvent mixture of dimethyl sulfoxide (DMSO) and chloroform ($CHCl_3$) combined to match the dielectric constant of dimethylformamide.

In some embodiments, the nanoparticle can contain additional surface-associated molecules which alter the properties or functions of the nanoparticles. Addition of surface-associated molecules is occasionally referred to as "surface decoration." For instance, cellular uptake (e.g. by keratinocytes) or tissue penetration in the oral epithelia by nanoparticles can be modified by attaching one or more mucoadhesive molecules to the surface of the nanoparticle. In some embodiments, the mucoadhesive molecule is a lectin, thiolated polymer (thiomer), alginate polyethylene glycol acrylate (alginate-PEGAc), poloxamer, or any combination thereof. Optionally, a nanoparticle may contain a mucous penetrating ligand. In some embodiments, the mucous penetrating ligand comprises low molecular weight polyethylene glycol (PEG). In some embodiments, mucous penetrating ligand comprises a PEG having a low molecular weight of 50 kDa or less, 40 kDa or less, 30 kDa or less, 20 kDa or less, 10 kDa or less, 5 kDa or less, 3 kDa or less, 2 kDa or less, 1 kDa or less, 0.5 kDa or less, 0.25 kDa or less, 0.1 kDa or less, or combinations thereof. A surface decoration molecule may be attached to the nanoparticle alone or in combination with other surface decoration molecules. For example, a nanoparticle may contain a mucoadhesive molecule, a mucous penetrating ligand, and other surface decorating molecules.

Molecules used for surface decoration can be attached to a nanoparticle via surface binding chemistries of the nanoparticle. Alternatively, surface decoration molecules can be attached by ligands which serve as linkers between the nanoparticle and the surface decoration molecule. As an example, a nanoparticle can be formed from carboxylic acid-functionalized PLGA, to which ligands may be attached by carbodiimide conjugation chemistries.

The nanoparticles can contain additional components, for example additional electrophilic mutagen scavengers. In some embodiments, the electrophilic mutagen scavengers comprise gallic or lipoic acid.

Nanoparticles may be formulated in a variety of vehicles suitable for delivery to a subject. Optionally, the nanoparticles are formulated in a pharmaceutically acceptable excipient. In some embodiments, the nanoparticles may be formulated in an oral rinse formulation. Oral rinse compositions and methods to make oral rinse compositions are well known in the art (see, e.g., U.S. Pat. No. 8,273,385 (Shine), US 2005/0031550 (Busch)). In some embodiments, the nanoparticles may be formulated in a troche formulation (e.g. lozenge). In some embodiments, the nanoparticles may be formulated in topical gel formulation. In some embodiments, the nanoparticles may be formulated in mucoadhesive patch formulation.

Nanoparticles may be formulated in a vehicle in a range of concentrations. Typically, the concentration of nanoparticles in a vehicle is a therapeutic amount when administered to a subject. In some embodiments, a vehicle may be formulated with nanoparticles at a concentration of at least 1 ppm, 5 ppm, 10 ppm, 25 ppm, 50 ppm, 100 ppm, 200 ppm, 300 ppm, 400 ppm, 500 ppm, 600 ppm, 700 ppm, 800 ppm, 900 ppm, 1,000 ppm, 1,500 ppm, 2,000 ppm, 5,000 ppm, 10,000 ppm, 50,000 ppm, or at least 100,000 ppm. In some embodiments, a vehicle may be formulated with nanoparticles at a concentration of less than 500,000 ppm, 100,000 ppm, 50,000 ppm, 10,000 ppm, 5,000 ppm, 2,000 ppm, 1,000 ppm, 900 ppm, 800 ppm, 700 ppm, 600 ppm, 500 ppm, 400 ppm, 300 ppm, 200 ppm, 100 ppm, 50 ppm, 25 ppm, or less than 10 ppm.

The concentration of nanoparticles in a vehicle can range from any of the minimum values described above to any of the maximum values described above, for example from about 1 ppm to about 500,000 ppm, from about 10 ppm to about 100,000 ppm, or from about 100 ppm to about 10,000 ppm. This list is intended to be merely exemplary, and any of numerous combinations of minimum and maximum values described above may be used as a range of concentration of nanoparticles in a vehicle.

Methods of Use

In one aspect of the invention, provided herein is a method of chemoprevention comprising: administering to a subject a nanoparticle composition in an amount sufficient to prevent the recurrence of a cancer, wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In another aspect, disclosed herein is a method of chemoprevention comprising: administering to a subject a nanoparticle composition in an amount sufficient to inhibit (prevent) the progression of a precancerous lesion to a cancer (or induce regression of the precancerous lesion), wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In one aspect of the invention, provided herein is a method of chemoprevention comprising: administering to a subject a nanoparticle composition in an amount sufficient to prevent the recurrence of an oral squamous cell carcinoma (OSCC), wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In another aspect, disclosed herein is a method of chemoprevention comprising: administering to a subject a nanoparticle composition in an amount sufficient to inhibit (prevent) the progression of a precancerous lesion to an oral squamous cell carcinoma (OSCC) (or induce regression of the precancerous lesion), wherein the nanoparticle composition comprises a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

In another aspect, provided herein are methods for improving oral health comprising: administering to a subject a nanoparticle composition comprising a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

The methods can include any herein disclosed nanoparticle composition comprising a Janus particle comprising at least two chemopreventive agents, wherein at least one of the chemopreventive agents is selected from the group consisting of freeze-dried black raspberries (BRB), a synthetic vitamin A analogue, N-acetylcysteine (NAC), and an anti-interleukin 6 agent.

The nanoparticle compositions can be administered in a method for a range of purposes and indications. In some embodiments, the methods include administering to a subject a nanoparticle composition as a chemopreventive. In some embodiments, the chemopreventive prevents, or is intended to prevent, periodontal disease or oral cancer. In some embodiments, the chemopreventive prevents, or is intended to prevent, oral squamous cell carcinoma (OSCC) development, progression, or recurrence. Examples of oral cancers include, but are not limited to, cancer of the lips, tongue, cheeks, floor of the mouth, hard and soft palate, sinuses, and pharynx (throat),In some embodiments, the methods include administering a nanoparticle composition to a subject to prevent progression or recurrence of periodontal disease (e.g. chronic, aggressive, and necrotizing periodontal disease, periodontitis manifesting from systemic diseases, gingivitis, gum recession, gingival recession, perio-endo lesion). This list of administration purposes and indications is non-exhaustive and merely for purposes of example only, and in some embodiments, the methods include administering to a subject a nanoparticle composition for any combination of the above or other purposes and indications.

One advantage of the presently disclosed methods is that the nanoparticles, and hence the chemopreventive agents, can be locally rather than systemically delivered. Local administration of therapeutic amounts of an agent typically reduces or eliminates deleterious side-effects while still providing therapeutic or chemopreventive benefit. For instance, local administration may require a lower overall dosage compared to systemic administration of the same agent. In some embodiments, the administering step results in fewer deleterious side-effects in the subject of the at least two chemopreventive agents, as compared to systemic administration of the same chemopreventive agents. Optionally, the administering step does not result in deleterious systemic side-effects in the subject of the at least two chemopreventive agents. In some embodiments, administration of nanoparticles comprising 4-HPR results in no detectable sera levels of 4-HPR.

In some embodiments, the nanoparticle compositions suppress DNA damage, for example by suppressing alkylating agent-mediated DNA damage. In some embodiments, the nanoparticle compositions modulate keratinocyte growth and/or differentiation. In some embodiments, the nanoparticle compositions inactivate a signaling kinase. In some embodiments, the nanoparticle compositions interfere with tumor invasion and migration, for example by interfering with cytoskeletal components necessary for invasion and migration.

In some embodiments, the nanoparticle composition is administered locally to the oral epithelia. In some embodiments, the nanoparticles are administered locally to specific anatomical sites of the oral cavity. Anatomical sites of the oral cavity include, but are not limited to, the hard palate, soft palate, tonsil, gingivae, upper and lower labial frenum, lingual frenulum, vestibule, oropharynx, maxillary tuberosity, anterior and posterior pillars of fauces, uvula, palatoglossal arch, palatopharyngeal arch, lips, pharynx, tongue, epiglottis, laryngopharynx, and cheek. Optionally, the nanoparticle composition is administered to the site of a previously resected oral squamous cell carcinoma (OSCC).

The nanoparticle composition is typically administered in an effective amount (e.g. in an amount sufficient to prevent cancer progression or recurrence). In some instances, the desired effect may also be achieved by altering the duration of time that the nanoparticle composition contacts the oral epithelia. Thus, in some embodiments, the contact time of the administration step can be for a duration sufficient to achieve an intended beneficial effect. As an example, the nanoparticle composition formulation (e.g. an oral rinse, troche, topical gel, mucoadhesive patch, etc.) may contact the oral epithelia (e.g. by gargle) for at least 1, 2, 3, 4, 5, 6, 7, 8, 9, 10, 15, 20, 25, 30, 45, or 60 seconds. Optionally, the nanoparticle composition formulation may contact the oral epithelia for up to 5, 10, 15, 20, 30, 45, or 60 minutes, or up to 2, 3, 4, 5, 6, 7, 8, 9, or 10 hours. Optionally, the nanoparticle composition formulation may contact the oral epithelia for less than 10, 9, 8, 7, 6, 5, 4, 3, 2, or less than 1 hour. Optionally, the nanoparticle composition formulation may contact the oral epithelia for less than 60, 45, 30, 15, 10, 9, 8, 7, 6, 5, 4, 3, 2, or less than 1 minute. The contact time can range from any of the minimum values described above to any of the maximum values described above, for example from about 1 second to about 10 hours, from about 1 minute to about 1 hour, or from about 5 minutes to about 30 minutes. This list is intended to be merely exemplary, and any of numerous combinations of minimum and maximum values described above may be used as a range of contact times.

In some embodiments, the administering step results in penetration of at least a portion of the administered chemopreventive agents through the oral epithelium. Optionally, chemopreventive agents can penetrate to the epithelium-facing surface of the basement membrane separating the oral epithelium from the lamina propia.

Administration of the nanoparticle compositions may provide a range of therapeutic benefits to the subject, including but not limited to, reduced DNA damage from alkylating agents, modulation of keratinocyte growth and differentiation, augmentation of cellular cytoprotection, tumor regression, OSCC prevention, and so forth.

The disclosed methods include administering to a subject a first dose of a nanoparticle composition. In some embodiments, one or more doses of a nanoparticle composition may be administered. Optionally, at least two doses of a nanoparticle composition can be administered (e.g. a first dose and a second dose). In some embodiments, at least three, four, five, six, seven, eight, nine, or ten doses of a nanoparticle composition are administered. Administration of the nanoparticle compositions can be carried out at dosages and for periods of time effective for chemoprevention in a subject. In some embodiments, the pharmacokinetic profiles of the systems of the present invention are similar for male and female subjects.

The method, in some embodiments, may further comprise monitoring disease status in the subject. For example, disease formation, progression, recession, maturation, malignancy, amelioration of symptoms, or any combination thereof can be observed and measured prior to, or at the time of, the administering step, and subsequently observed and measured again (e.g., at the time of or after the administering step). Comparisons of disease status in the subject before and after a first dose provides information useful for modifying subsequent dosages. Disease status can be monitored by any method known in the art to be effective for monitoring the particular disease. Known, non-limiting methods for monitoring diseases such as oropharyngeal cancer (e.g. OSCC) include physical and/or visual examination, tissue microsection or biopsy, endoscopy, imaging techniques, microbial swab, and combinations thereof.

The method, in some embodiments, may further comprise adjusting the concentration of nanoparticles in a second dose of a nanoparticle composition to be administered to a subject after a first dose of a nanoparticle composition is administered. Adjustment is typically based on outcomes from monitoring disease status. For example, the concentration of nanoparticles in a second dose may be increased when a subject exhibits a lack of improved disease symptoms or conditions after receiving a first dose. Alternatively, the concentration of nanoparticles in a second dose may be decreased when a subject exhibits improved disease symptoms or conditions after receiving a first dose. Optionally, the amount of chemopreventive agent loaded on nanoparticles may be adjusted instead of, or in addition to, adjusting the concentration of nanoparticles in a second or subsequent dose.

The methods provided herein can be combined with one or more additional treatments. In a preferred embodiment, the Janus nanoparticle formulations would be employed as secondary chemopreventive agents to prevent progression of premalignant oral epithelial lesions to overt OSCC. In the event of OSCC development, the nanoparticles could be employed as tertiary chemopreventives to prevent local OSCC recurrence at the surgical site or a second primary OSCC. Traditional oral chemotherapy includes, but is not limited to, cisplatin, carboplatin, 5-fluorouracil, paclitaxel, docetaxel, methotrexate, ifosfamide, bleomycin, and combinations thereof. As a result of locally administering the herein disclosed nanoparticles, additional treatments may be provided to a subject at lower dosages and/or fewer number of dosages. Additional treatments can be administered locally or systemically.

The subject can be any mammal, for example a human or other primate, a rabbit, a rodent such as a mouse, rat or guinea pig, a horse, livestock such as a cow, pig, or chicken, and others. The subject can be of any age, gender, weight, height, race, ethnicity, or other physical attributes.

In some embodiments, the subject is diagnosed with oral cancer. Oral cancer is oral squamous cell carcinoma about 90% of the time. Other cancers that happen in the mouth with are lymphoproliferative-hematopoietic (about 5%) and salivary gland cancers (about 5%). In some embodiments, the subject is diagnosed with oral squamous cell carcinoma (OSCC). In some embodiments, the subject can be at risk of cancer progression or recurrence, particularly oral cancer, particularly OSCC. In some embodiments, the subject is diagnosed as having Fanconi Anemia (FA).

The methods for improving oral health comprising administering to a subject a nanoparticle can comprise administering a Janus particle. Janus particles can be formed from any of the materials described herein appropriate for nanoparticle construction, for instance polymeric materials (e.g. polystyrene, polymethylacrylate, polybutadiene), metals and metal oxides (e.g. gold, manganese oxide, zinc oxide), crystalline materials such as silicon oxides, other materials, and mixtures thereof. In some embodiments, the Janus particle comprises poly(lactic-co-glycolic acid) (PLGA).

In some method embodiments, the nanoparticles may have a diameter of at least about 1 nm, 10 nm, 50 nm, 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 4000 nm, 5000 nm, 6000 nm, 7000 nm, 8000 nm, or at least 9000 nm. In some embodiments, the nanoparticles may have a diameter of less than 10,000 nm, 9000 nm, 8000 nm, 7000 nm, 6000 nm, 5000 nm, 4500 nm, 4000 nm, 3500 nm, 3000 nm, 2500 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 250 nm, or less than 100 nm.

The diameter of nanoparticles can range from any of the minimum values described above to any of the maximum values described above, for example from 1 nm to 10,000 nm, 50 nm to 5,000 nm, 100 nm to 2500 nm, 200 nm to 2000 nm, or 500 nm to 1000 nm. This list is intended to be merely exemplary, and any of numerous combinations of minimum and maximum values described above may be used as a range of nanoparticle diameters in a vehicle.

In some embodiments, the methods comprise administering nanoparticles having a monodispersed size distribution.

In some embodiments, the nanoparticles having a size of about 1 nm, 10 nm, 50 nm, 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 4000 nm, 5000 nm, 6000 nm, 7000 nm, 8000 nm, 9000 nm, or 10,000 nm.

In some embodiments, the at least two chemopreventive agents comprise BRB. Optionally, the black raspberries are *Rubus occidentalis*. In some embodiments, BRB comprises anthocyanins. In some embodiments, the anthocyanins comprise cyanidin-3-rutinioside cyanidin-3-glucoside, cyanidin-3-xylosylrutinoside, and cyanidin-3-sambuside. Optionally, isolated anthocyanins may substitute for BRB as a chemopreventive agent. For example, in some embodiments, nanoparticles can comprise an estimated dosage of 2-10 µmol/L cyanidin rutinoside as one of the at least two chemopreventive agents. In some embodiments, the at least two chemopreventive agents comprise a natural chemopreventive.

In some embodiments, the at least two chemopreventive agents comprise a synthetic vitamin A analogue. In some embodiments, the synthetic vitamin A analogue is fenretinide (4-HPR).

In some embodiments, the at least two chemopreventive agents comprise a thiol-sparing agent (e.g., N-acetylcysteine).

In some embodiments, the at least two chemopreventive agents comprise an anti-interleukin 6 (also referred to as anti-IL-6 or anti-IL6) agent. Anti-interleukin-6 agents include, but are not limited to, tocilizumab, situximab (Sylvant), sarilumab, olokizumab, elsilimomab, BMS-945429, sirukumab, and CPSI-2364. In some embodiments, the anti-IL-6 agent is an IL-6 receptor inhibitor. In some embodiments, the anti-IL-6 agent is an anti-IL-6 receptor antibody. In some embodiments, the anti-IL-6 receptor antibody is tocilizumab.

In some embodiments, the at least two chemopreventive agents comprise a biologic compound. Numerous other compounds, for example 2-methoxyestradiol, are naturally occurring angiogenic inhibitors. In some embodiments, 2-methoxyestradiol is administered in combination with at least one of the chemopreventive agents selected from the group consisting of freeze-dried black raspberries (BRB), a synthetic vitamin A analogue, N-acetylcysteine (NAC), and an anti-interleukin 6 agent.

The herein disclosed methods comprise administering a nanoparticle comprising at least two chemopreventive agents. In some embodiments, the chemopreventive agents selected are BRB and 4-HPR. In some embodiments, chemopreventive agents selected are 4-HPR and NAC. Optionally, the chemopreventive agents selected are 4-HPR and tocilizumab. Optionally, the chemopreventive agents selected are NAC and tocilizumab. Nanoparticles may contain any combination of up to all four of the chemopreventive agents BRB, 4-HPR, NAC, and tocilizumab. Further, nanoparticles may include additional chemopreventive agents, antimicrobial agents, targeting agents, and/or other surface decorating molecules, as discussed herein.

In some embodiments, the methods comprise administering nanoparticles comprising one or more additional chemopreventives, antimicrobial agents, and/or targeting agents. Suitable examples of additional chemopreventives, antimicrobial agents, and targeting agents are discussed within this application.

In some embodiments, the methods comprise administering a nanoparticle comprising at least two chemopreventive agents having a concentration ratio of about 1:1, 1:1.1, 1:1.2, 1:1.3, 1:1.4, 1:1.5, 1:1.6, 1:1.7, 1:1.8, 1:1.9, 1:2.0, 1:2.1, 1:2.2, 1:2.3, 1:2.4, 1:2.5, 1:2.6, 1:2.7, 1:2.8, 1:2.9, 1:3, 1:4, 1:5, 1:6, 1:7, 1:8, 1:9, 1:10, 1:20, 1:25, 1:30, 1:40, 1:50, 1:75, 1:100, 1:250, 1:500, 1:750, or 1:1,000. In embodiments of methods comprising administering nanoparticles having more than two chemopreventive agents, the above recited ratios may apply to any two of the more than two chemopreventive agents.

Optionally, the methods can include administering a nanoparticle loaded with at least 0.1, 0.5, 1, 2, 3, 4, 5, 6, 7, 8, 9, or 10 weight percent of a chemopreventive agent. In some embodiments, the nanoparticle can be loaded with at least 15, 20, 25, 30, 40, or 50 weight percent of a chemopreventive agent.

In some embodiments, the methods can include administering a nanoparticle having surface decoration. In some embodiments, the nanoparticle can include a mucoadhesive molecule, such as a lectin, thiolated polymer (thiomer), alginate polyethylene glycol acrylate (alginate-PEGAc), poloxamer, or any combination thereof. Alternatively, or in addition to a mucoadhesive molecule or other surface-associated molecules, a nanoparticle may contain a mucous penetrating ligand, such as a low molecular weight polyethylene glycol (PEG). In some embodiments, mucous penetrating ligand comprises a PEG having a low molecular weight 10 kDa or less, 5 kDa or less, 3 kDa or less, 2 kDa or less, 1 kDa or less, 0.5 kDa or less, 0.1 kDa or less, or combinations thereof. A surface decoration molecule may be attached to the nanoparticle alone or in combination with other surface decoration molecules. For example, a nanoparticle may contain a mucoadhesive molecule, a mucous penetrating ligand, and other surface decorating molecules.

Molecules used for surface decoration can be attached to a nanoparticle via surface binding chemistries of the nanoparticle. Alternatively, surface decoration molecules can be attached by ligands which serve as linkers between the nanoparticle and the surface decoration molecule. As an example, a nanoparticle can be formed from carboxylic acid-functionalized PLGA, to which ligands may be attached by carbodiimide conjugation chemistries.

Nanoparticles may be formulated in a variety of vehicles suitable for administration to a subject. In some embodiments, the nanoparticles may be administered in an oral rinse formulation, troche (e.g. lozenge) formulation, topical gel formulation, mucoadhesive patch formulation, or any combination thereof.

Nanoparticles may be formulated in a vehicle for administration to a subject in a range of concentrations. Typically, the concentration of nanoparticles in a vehicle is a therapeutic amount when administered to a subject. In some embodiments, a vehicle may be formulated with nanoparticles at a concentration of at least 1 ppm, 5 ppm, 10 ppm, 25 ppm, 50 ppm, 100 ppm, 200 ppm, 300 ppm, 400 ppm, 500 ppm, 600 ppm, 700 ppm, 800 ppm, 900 ppm, 1,000 ppm, 1,500 ppm, 2,000 ppm, 5,000 ppm, 10,000 ppm, 50,000 ppm, or at least 100,000 ppm. In some embodiments, a vehicle may be formulated with nanoparticles at a concentration of less than 500,000 ppm, 100,000 ppm, 50,000 ppm, 10,000 ppm, 5,000 ppm, 2,000 ppm, 1,000 ppm, 900 ppm, 800 ppm, 700 ppm, 600 ppm, 500 ppm, 400 ppm, 300 ppm, 200 ppm, 100 ppm, 50 ppm, 25 ppm, or less than 10 ppm.

The concentration of nanoparticles in a vehicle can range from any of the minimum values described above to any of the maximum values described above, for example from about 1 ppm to about 500,000 ppm, from about 10 ppm to about 100,000 ppm, or from about 100 ppm to about 10,000 ppm. This list is intended to be merely exemplary, and any of numerous combinations of minimum and maximum values described above may be used as a range of concentration of nanoparticles in a vehicle.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Figure 1B:
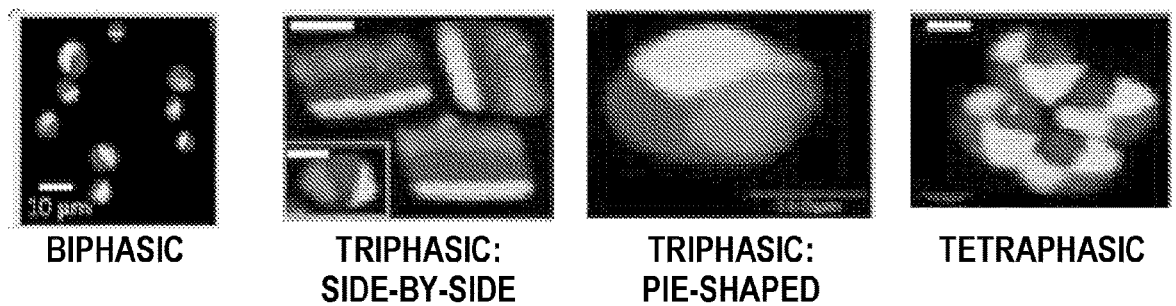
Figure 1C:
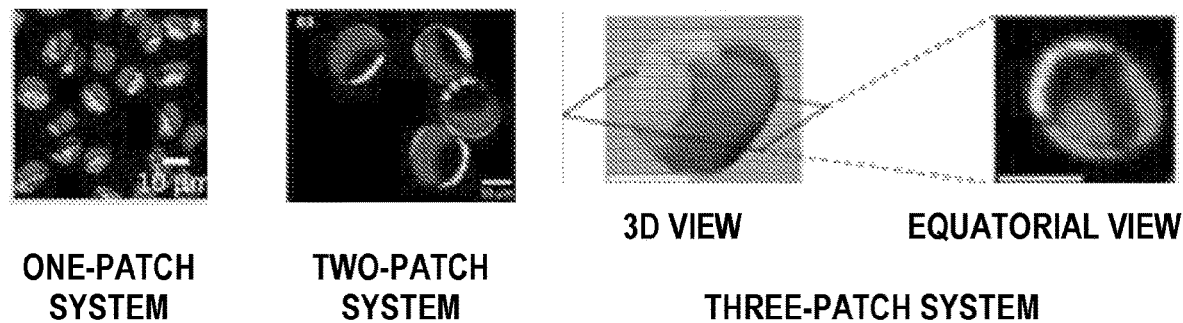
Figure 1D:
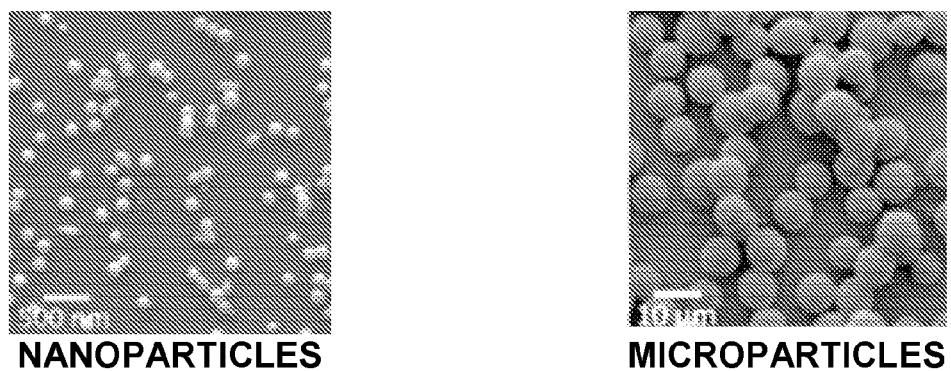
Figure 1E:
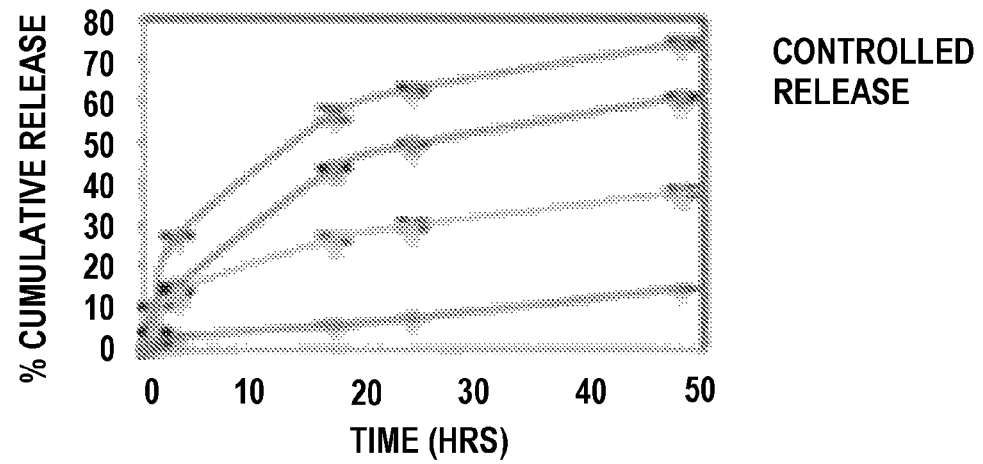
Figure 1E:
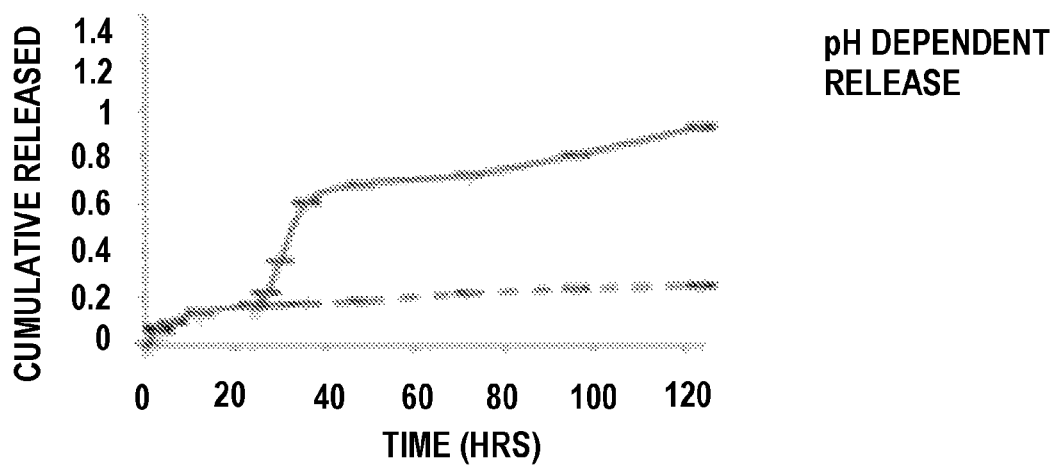

Example 1. Conceptual Development of Janus Particles Co-Loaded with Chemopreventive Agents Electrohydrodynamic (EHD) co-jetting may be used to create Janus particles with multiple distinct compartments composed of different matrix materials with various surface chemistry potentials and different payloads at defined ratios. EHD co-jetting involves the use of laminar flow of polymer solutions through two or more capillaries, and results in minimal mixing of the solutions at the tip of the needles. An electric field is applied to create a Taylor cone from the droplet at the tip of the needles, from which a steady jet of particles is produced (FIG. 1A). This technique allows for compartmentalization of the particles on which surface chemistries can be performed for each compartment. Two needles can be used during the fabrication process. By dissolving the compounds into the jetting solvents with the polymer, BRB (Berrihealth, Corvallis, Oreg.) is incorporated into one side of the nanoparticles and 4-HPR (MedChem Express, Monmouth Junction, N.J.; CAS65646-68-6) is incorporated into the other side. The agents' concentration in the jetting solution of each needle determines the BRB: 4-HPR ratio in the resulting nanoparticles and can be used to control the ratio delivered to the oral epithelia for synergistic effects. EHD co-jetting methods can result in nanoparticles having two, three, four, or more distinct surface chemistries to which different molecules (e.g., ligands, fluorescent reporters, antibodies, small molecules, etc.) can be attached in varying, controlled orientations (FIG. 1B). This permits distinct and controlled compartments having distinct surface chemistries and hence, distinct and controlled loaded molecules. In another embodiment, chemically distinct patches of the surface of the Janus particles are used to immobilize different biological binding moieties (FIG. 1C). In one example, modified PLGA polymers with alkyne, benzophenone, and carboxylic acid groups are used to immobilize three different binding ligands. Resultant particles can have diameters in the nanometer and/or micrometer range (FIG. 1D). Monodispersed populations of particles having similar diameters can be achieved after post-centrifugation collection (FIG. 1D, right panel). In yet another embodiment, distinct compartments of the Janus particles are comprised of polymers that degrade with different release kinetics and/or follow different resorption mechanisms. In one example (FIG. 1E), two compartments of a Janus particle each comprise distinct polymers comprising biodegradable polyesters (first compartment) and a rapidly resorbable dextran acetal (second compartment). At slightly acidic pH, the acetal groups of the dextran acetal polymer are hydrolytically cleaved resulting in rapid dissolution of the water-soluble product thereby releasing its payload. Meanwhile, release from the polyester compartment follows a distinct release mechanism wherein the payload is released with a slower release kinetic. In yet another example (FIG. 1E), the two compartments are both comprised of polyesters, but differences in molecular weight, additional additives, polymer hydrophilicity, etc. create distinct release kinetics between the two compartments.

Example 2. Preparation of Janus Particles Co-Loaded with Chemopreventive Agents

Janus particles were prepared by electrohydrodynamic co-jetting as described in Example 1. In this example, Janus particles were jetted with BRB in one compartment and 4-HPR in the other compartment, both at a loading of 10 weight percent. Particles were thoroughly dried under vacuum, collected in ultra-pure water, and analyzed and counted using dynamic light scattering and nanoparticle tracking analysis available in the University of Michigan Biointerfaces Institute. After jetting, a bimodal distribution of particle sizes results. In this example, diameters of BRB and 4-HPR co-loaded particles ranged from about 100 nm to about 5 μM (FIG. 2). Resultant size distribution can be separated by centrifugation.

Example 3. Effects of Chemopreventive Combination on Cellular Invasiveness

Basement membrane invasion is a key step in the transition from premalignant disease to overt OSCC. As an example of the combined effects of administration of two chemopreventive agents, the effects of BRB and 4-HPR, alone or in combination, on invasiveness of normal oral keratinocytes (EPI), and two OSCC cell lines (JSCC-2 and SCC2095sc) were determined using a synthetic basement membrane collagen IV coated Transwell membrane. Single treatment with BRB (10 μmon cyanidin rutinoside equivalent) significantly inhibited invasion in all groups, as compared to the empty vehicle. However, concurrent 4-HPR+ BRB treatment demonstrated additive (EPI and 2095sc) or synergistic (JSCC2) antiinvasive effects (n=8, mean+s.e.m., *=p<0.001; 2-way ANOVA, Bonferroni post hoc test). Thus, administration of the BRB+4-HPR combination is superior to the effects of either single chemopreventive agent alone with respect to inhibiting invasion of keratinocytes found in basement membranes.

Example 4. Human Enteric Recycling of Administered Chemopreventive Agents

Figure 3:
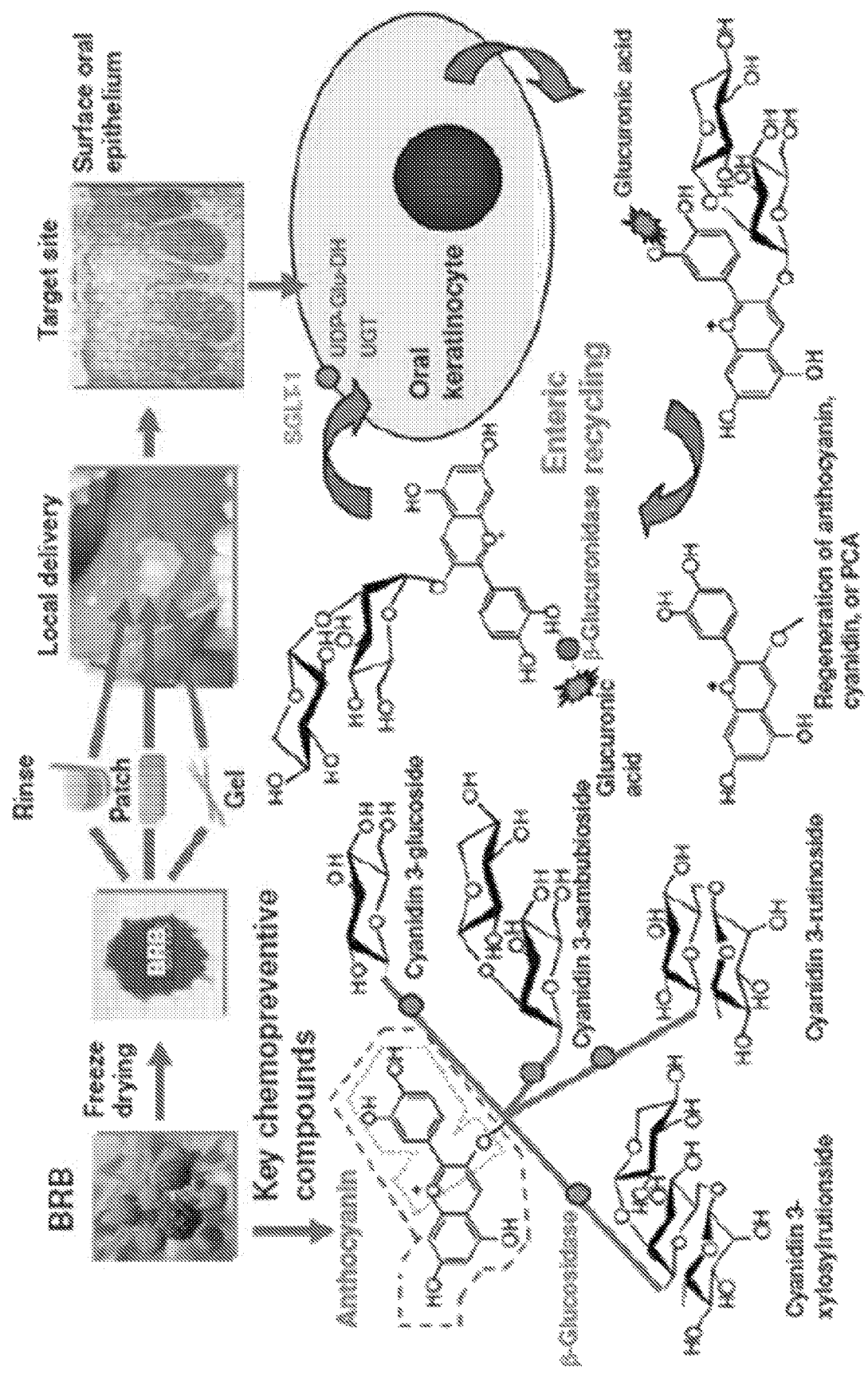
FIG. 3 is a schematic depicting the construction and oral delivery of BRB-containing nanoparticle formulations, and the presumed enteric metabolic recycling pathway for anthocyanins.

Anthocyanins provide the majority of BRB's chemopreventive effects. As shown in FIG. 3, freeze-drying black raspberries used to produce BRB retain active anthocyanins. BRB may be locally administered in the oral epithelium by several methods, including via oral rinse, patch, gel, troche, etc. The Janus particles allow for controlled release of proper ratios of chemopreventive agents at target sites in the surface oral epithelium.

Agent metabolism and tissue distribution also contribute to chemopreventive efficacy. Human oral epithelia possess the requisite enzymes necessary for local enteric recycling of BRB chemopreventive agents. The four primary BRB chemopreventive agents, cyanidin-3-rutinioside cyanidin-3-glucoside, cyanidin-3-xylosylrutinoside and cyanidin-3-sambuside, can be recycled in a metabolic loop in the oral epithelium. Without limiting to a particular exemplary pathway, it is suspected that oral keratinocytes internalize anthocyanins via sodium-dependent glucose cotransporters (e.g. SGLT-1) (FIG. 3). Secretion of glucuronic acid derivatives, enteric recycling of anthocyanins, cyanidins, or PCAs mediated by β-glucuronidase, and subsequent reuptake creates a metabolic loop which salvages anthocyanins from metabolic destruction. Thus, enteric recycling results in local tissue persistence of BRB chemopreventive agents.

Figure 4A:
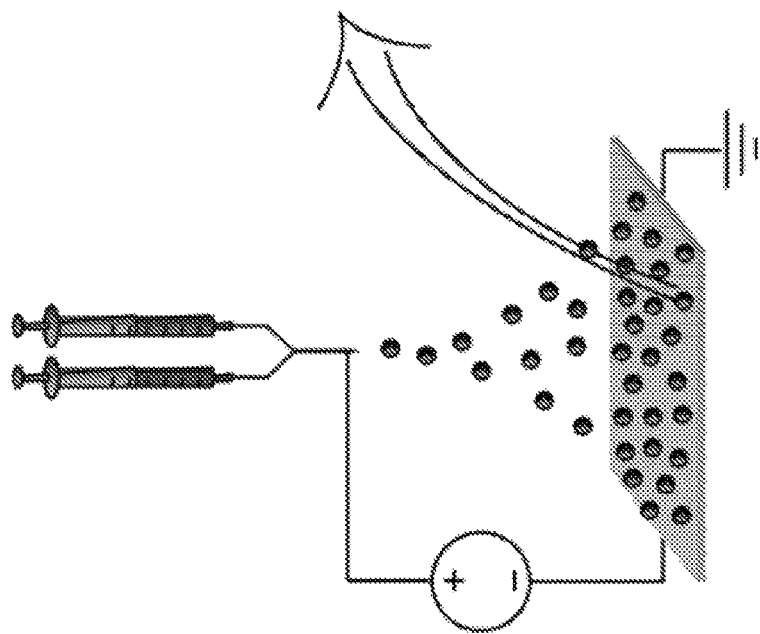
FIGS. 4A-4D show a schematic depicting the construction and properties of Janus particles.
Figure 4B:
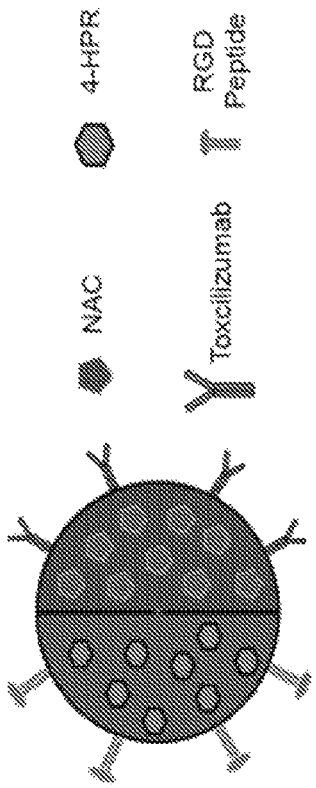
Figure 4C:
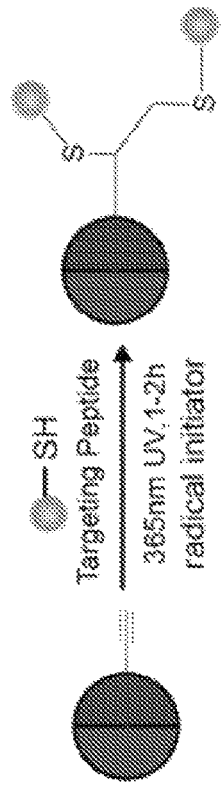
Figure 4D:
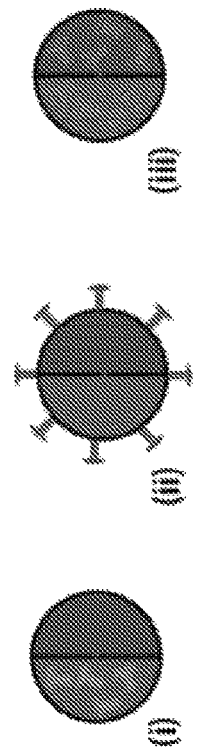
Figure 5A:
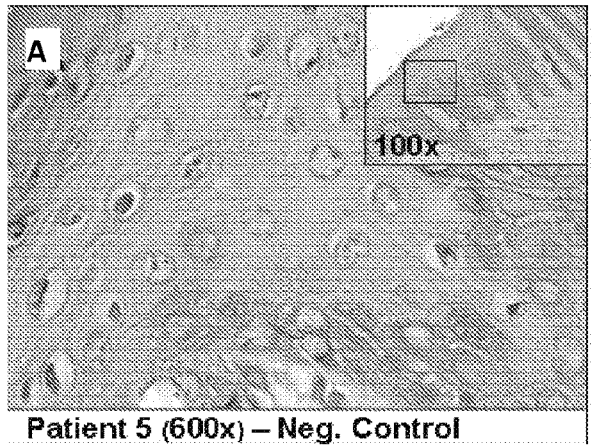
FIGS. 5A-5D depict nanoparticle uptake by intact human oral epithelium. Hematoxylin and eosin stained histologic sections in FIG. 5A (negative control, no nanoparticles) and FIG. 5B (other half of tissue section incubated with nanoparticles) depict (see arrows) nanoparticle penetration of the full thickness of the oral epithelial layers and penetration of the basement membrane.
Figure 5B:
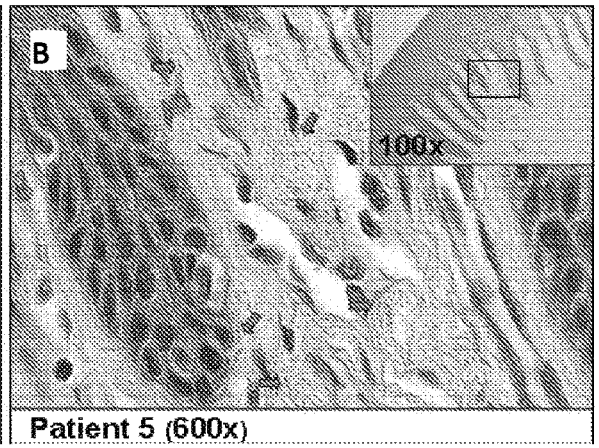
Figure 5C:
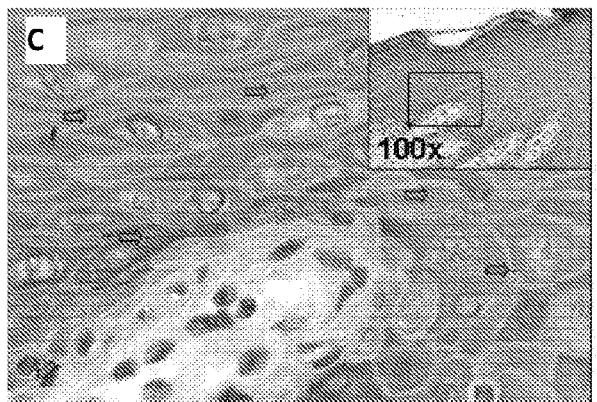
Figure 5D:
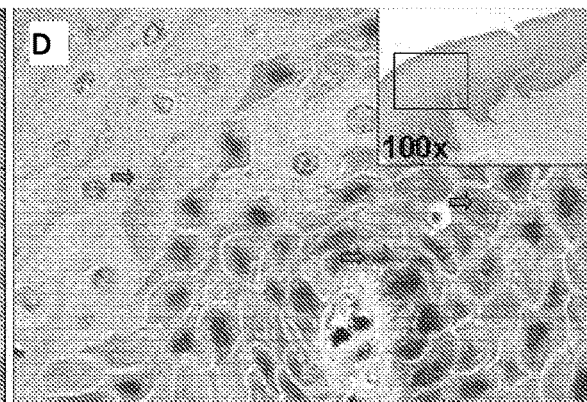
Figure 6A:
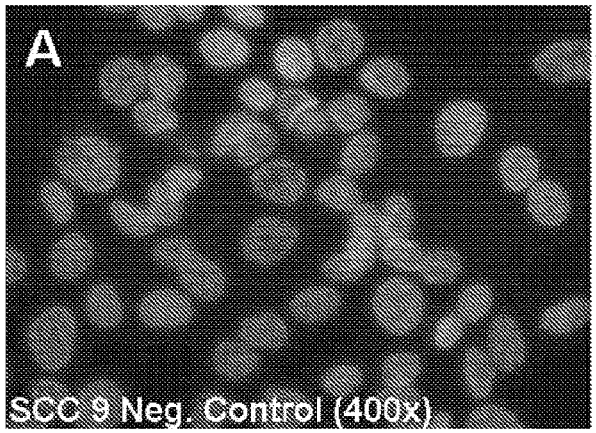
FIGS. 6A-6H depict nanoparticle uptake by the targeted cell population i.e. human oral keratinocytes. Representative photomicrographs are shown demonstrating nanoparticle internalization in monolayer cultured and STR validated human oral keratinocytes.
Figure 6B:
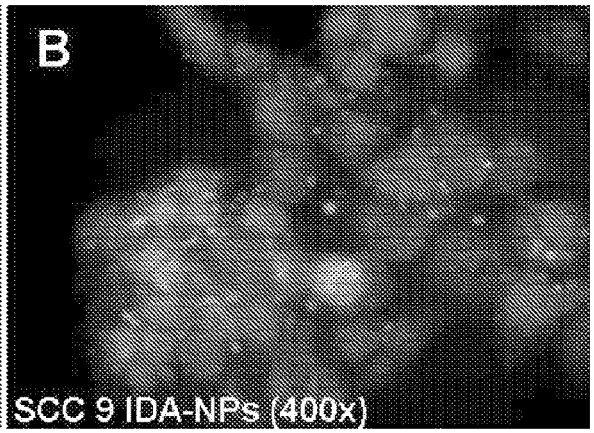
Figure 6C:
Figure 6D:
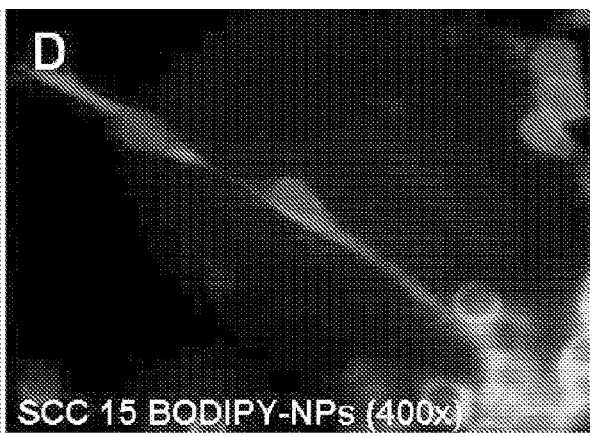
Figure 6E:
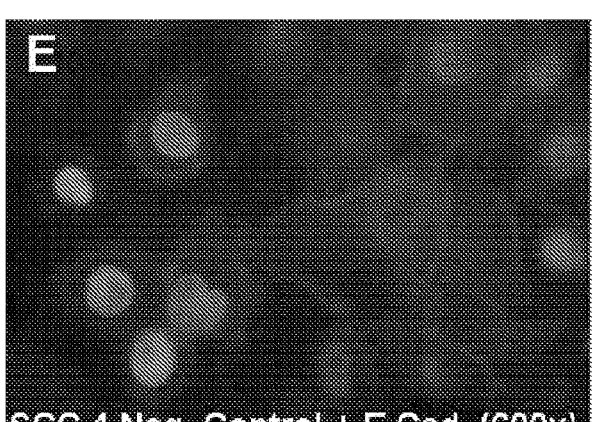
Figure 6F:
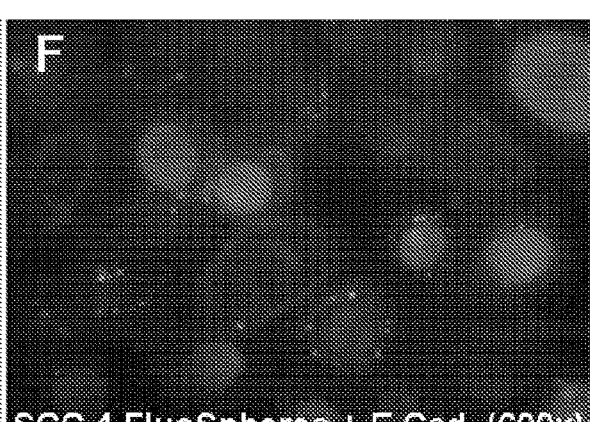
Figures 6G, 6H:
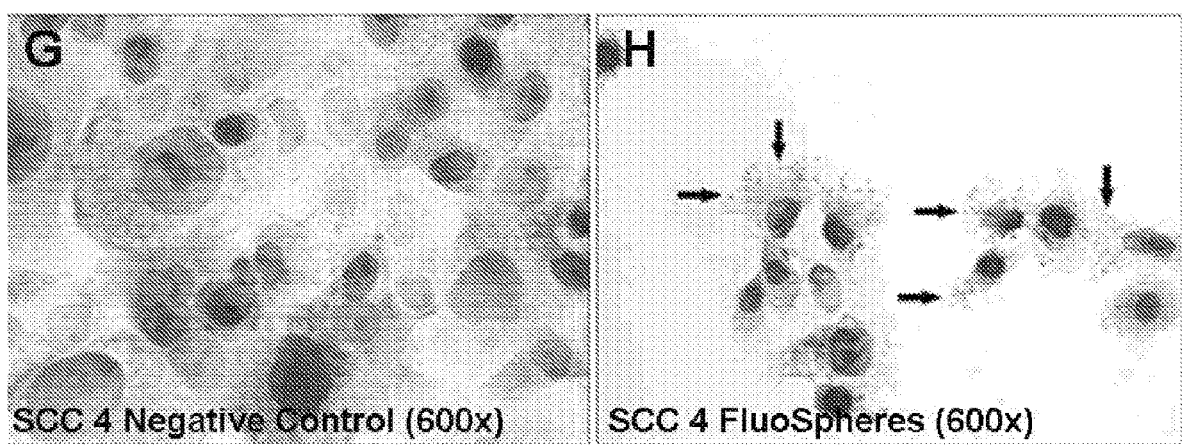
Figure 7:
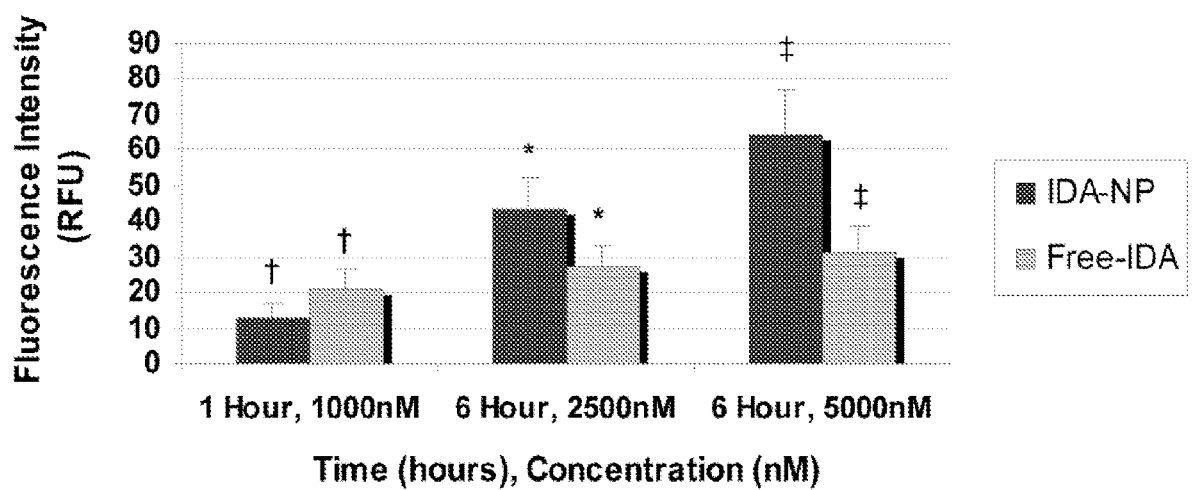
FIG. 7 depicts a bar graph of the cellular uptake (fluorescence intensity) of either nanoparticle vs. free probe over various times and concentrations, and demonstrates the nanoparticles' therapeutic advantage over bolus drug delivery towards achieving high intracellular drug levels. Mean±S.D., n=18, *=p<0.01, ‡=p,0.001, Mann Whitney U 2-tailed test.
Figure 8A:
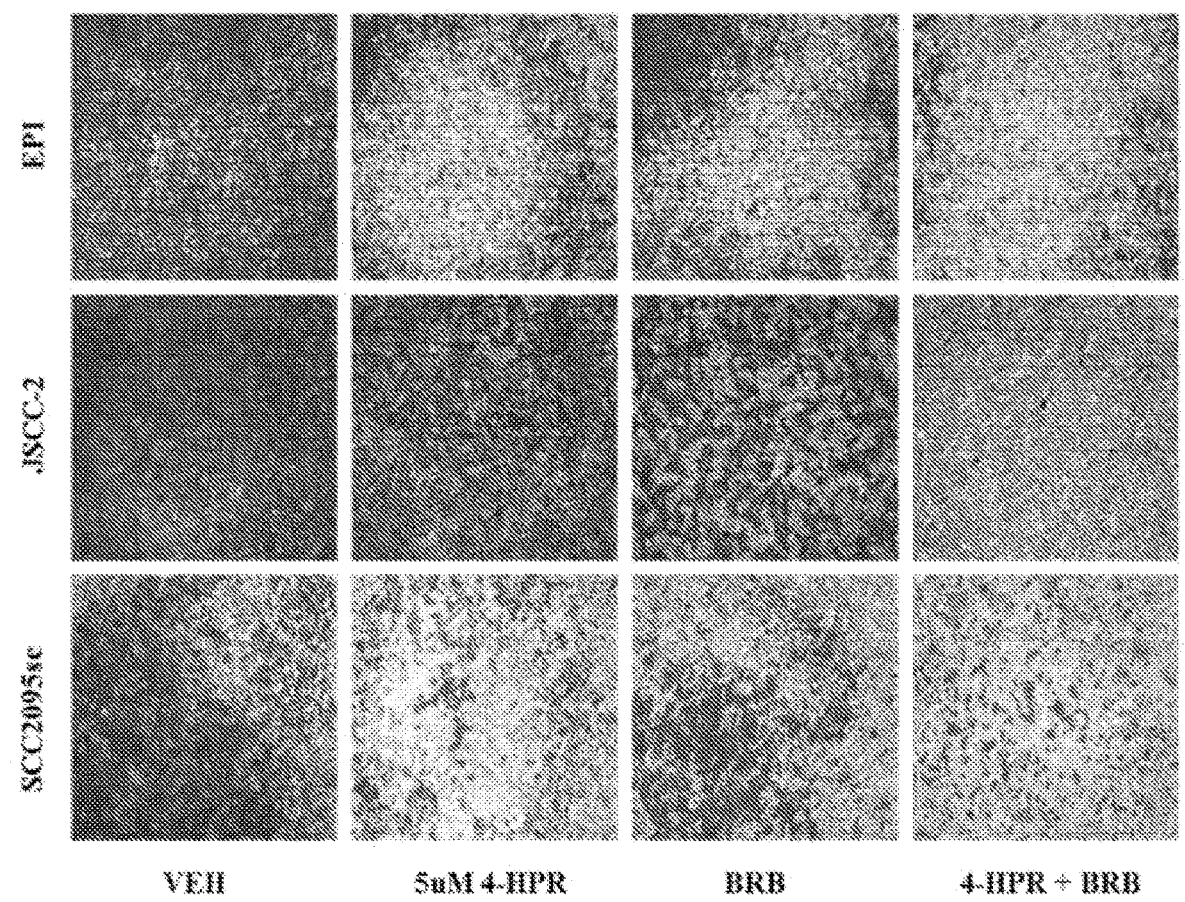
FIGS. 8A-8B demonstrate the effects of 4-HPR and BRB on human oral keratinocyte invasion of a synthetic basement membrane.
Figure 8B:
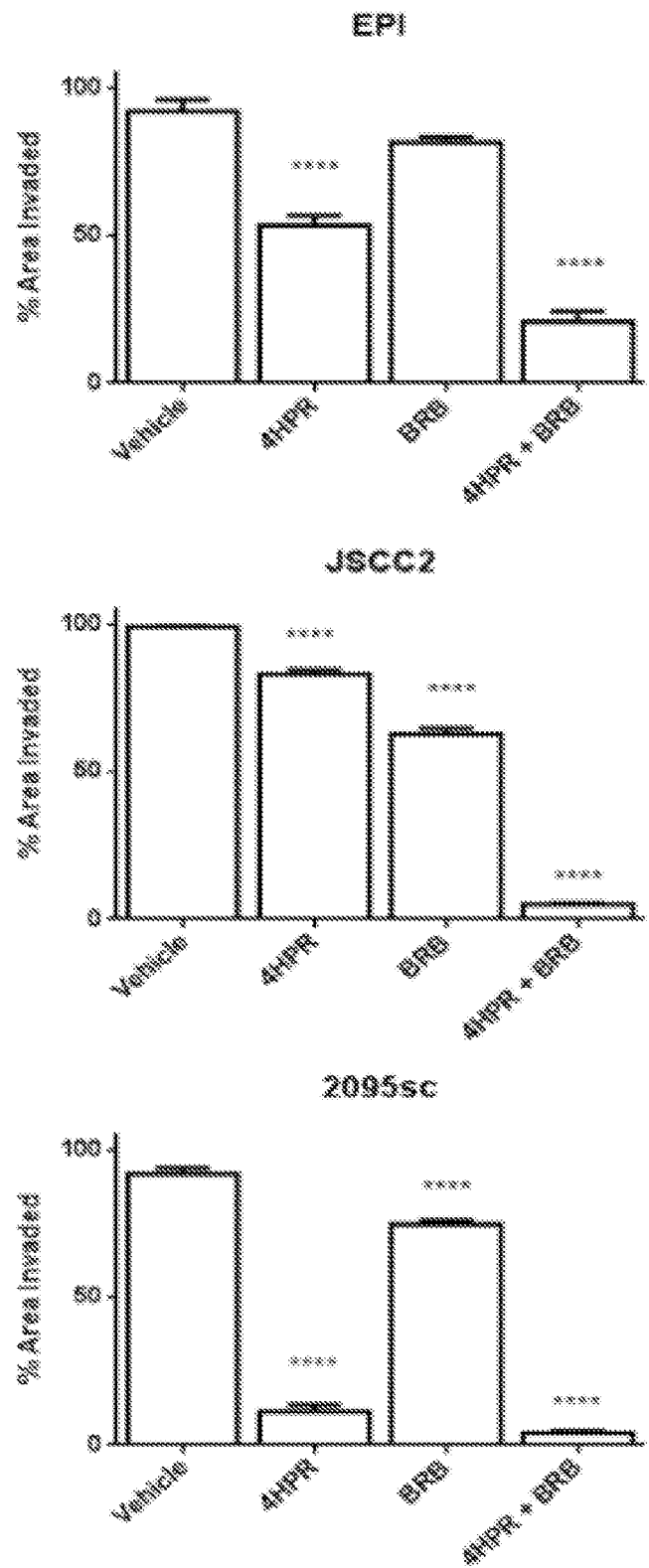

Example 5. EHD Co-Jetting and Formation of Compartmentalized Surface Chemistries Electrohydrodynamic (EHD) co-jetting technology provides a means to co-encapsulate a wide range of small molecules (therapeutics, fluorescent dyes) and biological compounds (peptides, RNA, DNA) with intrinsically different properties and pharmacokinetics into a single particle system. Distinct surface patches of a nanoparticle can be selectively modified using this method. For targeted FA therapy, the versatility of the EHD co-jetting process provides the ideal nanoparticle design platform to maximize the synergy of diverse treatment modalities. FIG. 4A shows a series of nanoparticles formed by EHD co-jetting, in which the separate hemispheres having distinct surface chemistries are derived from separate starting materials in separate needles. Nanoparticles formed by this method may have diameters in their hydrated state ranging across nanometer and micrometer ranges. In some instances and depending on the desired applications, nanoparticles can be selectively formed to have diameters in their hydrated state ranging from 200 to 500 nm. In addition to various drug combinations (FIG. 4B), Janus nanoparticles can also include Alexa Fluor 647 fluorescently tagged BSA (<1 w-%) for particle monitoring in subsequent delivery experiments. A nanoparticle library of the drug combinations 4-HPR-co-NAC, 4-HPR-co-tocilizumab, and NAC-co-tocilixumab can be synthesized and compared to single drug particles. In some examples (FIG. 4B-4D), the Janus particle can be comprised of two compartments wherein the first compartment is comprised of a dextran-acetal, a first agent (e.g., 4-HPR), and the surface is modified with an epithelial cell targeting motif (RGD). The second compartment can be comprised of a PLGA matrix that encapsulates a second agent (e.g., NAC) and is decorated with an active ligand, tocilizumab, that interacts with surface-receptors of target cells. The surface ligands can be conjugated to reactive groups in the respective compartments using conjugation strategies known to someone skilled in the art, including, but not limited to thiol-ene reactions (FIG. 4C). Reconfiguration of the fluids used for particle preparation during electrohydrodynamic co-jetting leads to alternate formulations of therapeutic Janus particles without changing the fundamental preparation process (FIG. 4E).

Example 6. Oral Epithelial Tissue Internalizes Particles

FluoSphere penetration is shown in FIGS. 5A-5D in representative samples of intact normal oral stratified squamous epithelium. Following an elective oral surgical procedure, normal oral mucosa was collected and bisected (n=10 samples). One half of the full-thickness mucosal tissue was used as an explant-matched negative control (FIG. 5A), which was incubated in the absence of FluoSpheres. The other half of the matched mucosal tissue was used for the analysis of FluoSphere penetration and internalization (FIG. 5B), as described above. As demonstrated by the arrows (FIG. 5B), the nanoparticles penetrate the full thickness of oral epithelial layers and basement membrane. Furthermore, immunohistochemical stains of FluoSphere treated explants demonstrate full epithelial penetration and intracellular retention of nanoparticles in MRP1 (FIG. 5C) and BCRP (FIG. 5D) expressing tissue.

Representative photomicrographs of solid lipid nanoparticles (SLN) and FluoSphere internalization studies in monolayer-cultured human OSCC cells are shown in FIGS. 6A-6H. (FIG. 6A) Idarubicin-nanoparticle (IDA-NP) internalization negative control; cells were not treated with SLNs. Nuclei (blue) were stained with 300 nM DAPI. (FIG. 6B) SCC4, SCC9, and SCC15 cells internalized IDA-NPs (green) following 30-minute incubation with 2500 nM IDA-NPs (only SCC9 shown). (FIG. 6C) BODIPY-NP internalization negative control. (FIG. 6D) SCC4 and SCC15 cells internalized BODIPY-NPs (green) following 6-hour incubation with 1 µg BODIPY-NPs and subsequent quenching of extracellular fluorescence with 0.08% Trypan blue (only SCC15 shown). (FIG. 6E) FluoSphere internalization negative control with E-cadherin (to delineate cell boundaries) immunofluorescent staining. (FIG. 6F) SCC4 cells internalized FluoSpheres (green) following 2-hour incubation with $1.0 \times 10^7$ FluoSpheres. (FIG. 6G) FluoSphere immunocytochemistry negative control. (FIG. 6H) Immunocytochemistry evaluation of SCC4 cell internalization of FluoSpheres (arrows) to confirm size consistency utilizing both fluorescence and immunocytochemical analyses.

Idarubicin-nanoparticle delivery provided higher, sustained levels of intracellular idarubicin relative to free-idarubicin delivery in human OSCC cells. The internalization of free-IDA was more rapid than IDA-NP after 1-hour at 1000 nM (free-IDA: 21.08±5.33 vs. IDA-NP: 12.87±4.32). However, the maximum uptake of IDA-NP was greater than free-IDA after 6 hours at 2500 nM (IDA-NP: 43.53±8.42 vs. free-IDA: 27.61±5.66) and 5000 nM (IDA-NP: 64.44±12.71 vs. free-IDA: 31.06±7.24). [Data collected from three oral SCC cell lines, mean±SD, n=18, *P≤0.01 †P≤0.002, ‡P≤0.001; IDA-NP samples compared to free-IDA samples [Mann-Whitney U two-tailed Test].

Example 7. Functional Explant and Pharmacokinetic Analyses of Nanoparticles

For explant studies, Fanconi Anemia (FA) organotypic raft cultures with and without NAC supplementation are challenged with an aziridine alkylating agent (e.g., mitomycin C). DNA damage is assessed via the Gamma H2AX pharmacodynamics assay (Trevigen, assay suitable for cells and tissues). This assay is a sensitive indicator of an early cell response the double strand DNA breaks e.g., H2AX serine139 phosphorylation. While not likely to be highly problematic in FA cells, ongoing DNA repair can complicate assays to assess DNA damage. Assays are conducted in FANCD1 deficient raft cultures, as FANCD1 regulates a key component in repair of double strand DNA breaks (RAD 51 recombinase). FA raft cultures that contain other FA gene mutations are evaluated. FA raft culture (with and without NAC supplementation) DNA damage is reported as extent of γ-H2AX serine phosphorylation/mg sample protein.

For in vivo pharmacokinetic and oral epithelial assessment assays, the animal handling, anesthesia, tissue sampling, and determination of effects of 4-HPR on oral epithelial histology, growth state is described. Following a 7-day acclimation, rabbits are sedated with a subcutaneous injection (0.2 cc) of acepromazine (2 mg/ml, Butler Schein Animal Health, Dublin, Ohio) and placed under general anesthesia via isoflurane inhalation (2-3 vol/vol %) for the entire Janus NP (released from a mucoadherent gel dispersed throughout the mouth) exposure. Once unconscious and prior to gel-Janus NP exposure, 0.5 cc of blood is collected from the central ear artery. Gel-Janus NP is left in place for 10 minutes (~time for troche to dissolve), excess gel removed, and the surface epithelia lavaged with 200 µl of PBS for the gel-mucosal interface sample. After 10 days of treatment, sedated rabbits are sacrificed by deep anesthesia followed by intravenous KCl. Oral mucosal biopsies are sectioned into 2 pieces for LC-MS/MS analysis (stored in stabilizing buffer protected from light) and histology and IHC analyses. 4-HPR and metabolite levels are also evaluated in sera samples.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment(s) disclosed herein contemplated for carrying out this invention, but that the invention will include all embodiments falling within the scope of the claims.

Publications cited herein are hereby specifically incorporated by reference in their entireties and at least for the material for which they are cited.

We claim:

1. A nanoparticle composition comprising a Janus particle comprising:
   a first compartment comprising a first chemopreventive agent; and
   a second compartment comprising a second chemopreventive agent,
   wherein at least one of the first or second chemopreventive agents is selected from the group consisting of freeze-dried black raspberries (BRB), a synthetic vitamin A analogue, N-acetylcysteine (NAC), and an anti-interleukin 6 agent,
   wherein the first and second compartments are compositionally distinct, and
   wherein the nanoparticle composition exhibits a controlled release of the first and second chemopreventive agents in vivo.

2. The nanoparticle composition of claim 1, wherein the at least two chemopreventive agents selected are BRB and fenretinide (4-HPR).

3. The nanoparticle composition of claim 1, wherein the at least two chemopreventive agents selected are fenretinide (4-HPR) and NAC.

4. The nanoparticle composition of claim 1, wherein the at least two chemopreventive agents selected are fenretinide (4-HPR) and tocilizumab.

5. The nanoparticle composition of claim 1, wherein the at least two chemopreventive agents selected are NAC and tocilizumab.

6. The nanoparticle composition of claim 1, wherein the Janus particle comprises poly(lactic-co-glycolic acid).

7. The nanoparticle composition of claim 2, wherein the concentration ratio of BRB and 4-HPR is between 1:1 and 1,000:1.

8. The nanoparticle composition of claim 1, further comprising a mucoadhesive.

9. The nanoparticle composition of claim 8, wherein the mucoadhesive comprises lectin.

10. The nanoparticle composition of claim 1, further comprising a mucous penetration enhancer.

11. The nanoparticle composition of claim 10, wherein the mucous penetration enhancer comprises polyethylene glycol.

12. The nanoparticle composition of claim 1, wherein the at least two chemopreventive agents comprise a first chemopreventive agent and a second chemopreventive agent, wherein the nanoparticle comprises at least 10 weight percent of the first chemopreventive agent and at least 10 weight percent of the second chemopreventive agent.

13. The nanoparticle composition of claim 1, wherein the Janus particle further comprises:
 a third compartment comprising a third chemopreventive agent,
 wherein the third compartment is compositionally distinct from the first and second compartments.

14. The nanoparticle composition of claim 1, wherein at least one of the first compartment or the second compartment has a matrix comprising a polymer, a metal, a metal oxide, a crystalline material, or combinations thereof.

15. The nanoparticle composition of claim 1, wherein at least one of the first compartment or the second compartment has a matrix comprising a polymer selected from the group consisting of polymethylacrylate, polybutadiene, poly(lactic-co-glycolic acid) (PLGA), and combinations thereof.

16. The nanoparticle composition of claim 1, wherein at least one of the first compartment or the second compartment comprises a polyester matrix.

17. An oral rinse formulation comprising the nanoparticle composition of claim 1.

18. A troche formulation comprising the nanoparticle composition of claim 1.

19. A topical gel formulation comprising the nanoparticle composition of claim 1.

20. A mucoadhesive patch formulation comprising the nanoparticle composition of claim 1.

21. A method for improving oral health comprising: administering to a subject the nanoparticle composition of claim 1.

22. A method of chemoprevention comprising: administering to a subject the nanoparticle composition of claim 1 in an amount sufficient to treat the recurrence of a cancer.

23. The method of claim 22, wherein the cancer is oral squamous cell carcinoma (OSCC).

24. The method of claim 22, wherein the subject is diagnosed as having Fanconi Anemia.

* * * * *